(12) United States Patent
Meyer et al.

(10) Patent No.: US 8,114,971 B2
(45) Date of Patent: *Feb. 14, 2012

(54) **NUCLEIC ACID MOLECULES ENCODING PROTEINS WHICH IMPART THE ADHESION OF *NEISSERIA* CELLS TO HUMAN CELLS**

(75) Inventors: Thomas F. Meyer, Tubingen (DE); Thomas Rudel, La Jolla, CA (US); Ina Scheuerpflug, Berlin (DE); Jurgen Maier, Kongen (DE); Sandra Eickernjager, Berlin (DE); Thomas Schwan, Berlin (DE); Eckhard Fischer, Tübingen (DE)

(73) Assignee: Max-Planck Gesellschaft zur Forderung der Wissenschaften E.V., Berlin (DE)

( * ) Notice: Subject to any disclaimer, the term of this patent is extended or adjusted under 35 U.S.C. 154(b) by 1319 days.

This patent is subject to a terminal disclaimer.

(21) Appl. No.: 11/797,464

(22) Filed: May 3, 2007

(65) Prior Publication Data

US 2008/0200665 A1    Aug. 21, 2008

Related U.S. Application Data

(62) Division of application No. 10/617,835, filed on Jul. 14, 2003, now abandoned, which is a division of application No. 09/043,302, filed as application No. PCT/EP96/04092 on Sep. 18, 1996, now Pat. No. 6,617,128.

(30) Foreign Application Priority Data

Sep. 18, 1995 (DE) .................................. 195 34 579

(51) Int. Cl.
*C07H 21/04* (2006.01)
*C12N 15/00* (2006.01)
*A01N 63/00* (2006.01)
*A61K 48/00* (2006.01)

(52) U.S. Cl. .................... 536/23.1; 435/320.1; 424/93.2

(58) Field of Classification Search ........................ None
See application file for complete search history.

(56) References Cited

U.S. PATENT DOCUMENTS 5,912,336 A    6/1999  Sparling et al.

FOREIGN PATENT DOCUMENTS

DE              4336530 C        4/1995
WO           WO-9213871          8/1992

OTHER PUBLICATIONS

Biswas, et al. (Aug. 1995) "Characterization of IbpA, the Structural Gene for a Lactoferrin Receptor in *Neisseria gonorrhoeae*", Infection and Immunity, 63(8): 2958-67.*
Paruchuri, D. et al PNAS, USA, Bd.87, Nr. 1, Jan. 1990, 333-337.
Nassif et al. Clinical Microbiology Reviews, Bd. 8, Nr. 3, Jul. 1995, p. 376-388, XP000644345.
Morand et al. The EMBO Journal 23(9): 2009-2017,2004.
Ngo, in The Protein Folding Problem and Tertiary Structure Prediction, Merz et al. (eds.), Birkhauser Boston: Boston, MA, pp. 433 and 492-495,1994.
Rudinger (in Peptide Hormone, Parsons ed.), University Park Press: Baltimore, MD pp. 1-7,1976.

* cited by examiner

*Primary Examiner* — Robert M Kelly
(74) *Attorney, Agent, or Firm* — Birch, Stewart, Kolasch & Birch, LLP

(57) ABSTRACT

Described are nucleic acid molecules encoding proteins mediating the adhesion of bacteria of the genus *Neisseria* to human cells. Also described are the proteins encoded by these nucleic acid molecules and antibodies directed against them. Furthermore, pharmaceutical compositions, vaccines and diagnostic compositions containing the nucleic acid molecules, proteins and/or antibodies are described.

10 Claims, 4 Drawing Sheets

Figure 1:
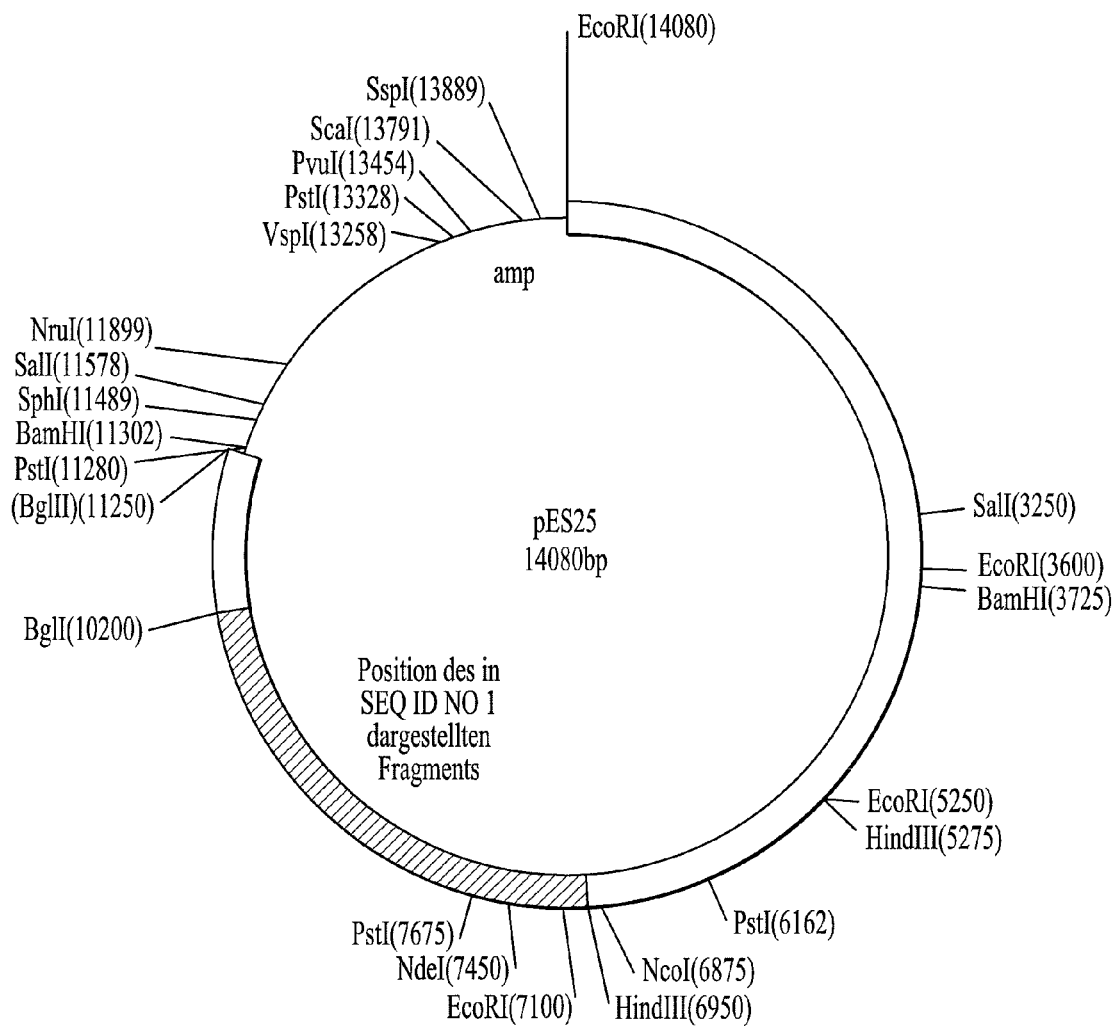

```
                1 (BglI)
                CCGGCGCAAACGGCGGACGCTGCTGTTAGCCCCGCTTGAAACAAATGC      47
         -35              -10
CGTCTGAACGCCACTTCAGACGGCATTTTTATAATAAGGCGCTGTCCTAGATAACTAGGG    107
                          S.D.
AAATTCAAATTAAGTTAGAATTATCCCTATGAGAAAAAGCCGTCTAAGCCGGTATAAACA    167
                                    M  R  K  S  R  L  S  R  Y  K  Q
AAATAAACTCATTGAACTGTTTGTCGCAGGCGTAACTGCAAGAACAGCAGCAGAGCCTGA    227
 N  K  L  I  E  L  F  V  A  G  V  T  A  R  T  A  A  E  P  D
CAGCATTGTTTATACGGATTGTTATCGTCGCTATGATGTATTGGATGCGGGCGAATTTAG    287
 S  I  V  Y  T  D  C  Y  R  R  Y  D  V  L  D  A  G  E  F  S
CCATTTCCGTATCAATCACAGCACACATTTTGCCGAACGACAAAACCATATTAATGGAAT    347
 H  F  R  I  N  H  S  T  H  F  A  E  R  Q  N  H  I  N  G  I
TGGGAACTTTTGGAACCGGGCAAAACGTCATTTACGCAAGTTTGACGGCATTCCCAAAGA    407
 G  N  F  W  N  R  A  K  R  H  L  R  K  F  D  G  I  P  K  E
GCATTTTGAGCCGTATTTAAAGGAGTGCGAACGGCGTTTTTAACAACAGTGAGATAAAAG    467
 H  F  E  P  Y  L  K  E  C  E  R  R  F  *
                                          -35
TTCTTGTTCCATTTTAAAACAATTAGTAAAATCGAGTTTATCCTAGTTGTCCAGGACGGC    527
    -10                                      S.D.
CCCTAATTTATTTACAATTTTGATACAATTTGTTTTTCATCAAAGGAGAAAATCTATGCG    587
                                                           M  R
GGCACGGCTGCTGATACCTATTCTTTTTTCGGTTTTTATTTTATCCGCCTGCGGGACACT    647
 A  R  L  L  I  P  I  L  F  S  V  F  I  L  S  A  C  G  T  L
                                                     A
GACAGGTATTCCATCGCATGGCGGAGGCAAACGCTTCGCGGTCGAACAAGAACTTGTGGC    707
 T  G  I  P  S  H  G  G  G  K  R  F  A  V  E  Q  E  L  V  A
CGCTTCTGCCAGAGCTGCCGTTAAAGACATGGATTTACAGGCATTACACGGACGAAAAGT    767
 A  S  A  R  A  A  V  K  D  M  D  L  Q  A  L  H  G  R  K  V
TGCATTGTACATTGCAACTATGGGCGACCAAGGTTCAGGCAGTTTGACAGGGGGTCGCTA    827
 A  L  Y  I  A  T  M  G  D  Q  G  S  G  S  L  T  G  G  R  Y
CTCCATTGATGCACTGATTCGCGGCGAATACATAAACAGCCCTGCCGTCCGCACCGATTA    887
 S  I  D  A  L  I  R  G  E  Y  I  N  S  P  A  V  R  T  D  Y
CACCTATCCGCGTTACGAAACCACCGCTGAAACAACATCAGGCGGTTTGACGGGTTTAAC    947
 T  Y  P  R  Y  E  T  T  A  E  T  T  S  G  G  L  T  G  L  T
CACTTCTTTATCTACACTTAATGCCCCTGCACTCTCGCGCACCCAATCAGACGGTAGCGG   1007
 T  S  L  S  T  L  N  A  P  A  L  S  R  T  Q  S  D  G  S  G
```

Fig.2A

```
AAGTAGGAGCAGTCTGGGCTTAAATATTGGCGGGATGGGGGATTATCGAAATGAAACCTT  1067
 S  R  S  S  L  G  L  N  I  G  G  M  G  D  Y  R  N  E  T  L
GACGACCAACCCGCGCGACACTGCCTTTCTTTCCCACTTGGTACAGACCGTATTTTTCCT  1127
 T  T  N  P  R  D  T  A  F  L  S  H  L  V  Q  T  V  F  F  L
GCGCGGCATAGACGTTGTTTCTCCTGCCAATGCCGATACAGATGTGTTTATTAACATCGA  1187
 R  G  I  D  V  V  S  P  A  N  A  D  T  D  V  F  I  N  I  D
CGTATTCGGAACGATACGCAACAGAACCGAAATGCACCTATACAATGCCGAAACACTGAA  1247
 V  F  G  T  I  R  N  R  T  E  M  H  L  Y  N  A  E  T  L  K
AGCCCAAACAAAACTGGAATATTTCGCAGTAGACAGAACCAATAAAAAATTGCTCATCAA  1307
 A  Q  T  K  L  E  Y  F  A  V  D  R  T  N  K  K  L  L  I  K
ACCCAAAACCAATGCGTTTGAAGCTGCCTATAAAGAAAATTACGCATTGTGGATGGGGCC  1367
 P  K  T  N  A  F  E  A  A  Y  K  E  N  Y  A  L  W  M  G  P
GTATAAAGTAAGCAAAGGAATCAAACCGACGGAAGGATTAATGGTCGATTTCTCCGATAT  1427
 Y  K  V  S  K  G  I  K  P  T  E  G  L  M  V  D  F  S  D  I
CCGGCCATACGGCAATCATACGGGTAACTCCGCCCCATCCGTAGAGGCTGATAACAGTCA  1487
 R  P  Y  G  N  H  T  G  N  S  A  P  S  V  E  A  D  N  S  H
TGAGGGGTATGGATACAGCGATGAAGCAGTGCGACAACATAGACAAGGGCAACCTTGATT  1547
 E  G  Y  G  Y  S  D  E  A  V  R  Q  H  R  Q  G  Q  P  *
                                                   S.D.
CACACTGCCATAACCGCTTGCTGCCAAGGAAAACAAAATGAATTTGCCTATTCAAAAATT  1607
                                  M  N  L  P  I  Q  K  F
                                                        ↑
CATGATGCTGTTTGCAGCGGCAATATCGTTGCTGCAAATCCCCATTAGTCATGCGAACGG  1667
 M  M  L  F  A  A  A  I  S  L  L  Q  I  P  I  S  H  A  N  G
       ↑
TTTGGATGCCCGTTTGCGCGATGATATGCAGGCAAAACACTACGAACCGGGTGGCAAATA  1727
 L  D  A  R  L  R  D  D  M  Q  A  K  H  Y  E  P  G  G  K  Y
CCATCTGTTCGGTAATGCTCGCGGCAGTGTTAAAAATCGGGTTTGCGCCGTCCAAACATT  1787
 H  L  F  G  N  A  R  G  S  V  K  N  R  V  C  A  V  Q  T  F
TGATGCAACTGCGGTCGGCCCCATACTGCCTATTACACACGAACGGACAGGGTTTGAAGG  1847
 D  A  T  A  V  G  P  I  L  P  I  T  H  E  R  T  G  F  E  G
CATTATCGGTTATGAAACCCATTTTTCAGGACACGGACACGAAGTACACAGTCCGTTCGA  1907
 I  I  G  Y  E  T  H  F  S  G  H  G  H  E  V  H  S  P  F  D
TAATCATGATTCAAAAAGCACTTCTGATTTCAGCGGCGGCGTAGACGGCGGTTTTACCGT  1967
 N  H  D  S  K  S  T  S  D  F  S  G  G  V  D  G  G  F  T  V
TTACCAACTTCATCGGACAGGGTCGGAAATACATCCCGCAGACGGATATGACGGGCCTCA  2027
 Y  Q  L  H  R  T  G  S  E  I  H  P  A  D  G  Y  D  G  P  Q
AGGCGGCGGTTATCCGGAACCACAAGGGGCAAGGGATATATACAGCTACCATATCAAAGG  2087
 G  G  G  Y  P  E  P  Q  G  A  R  D  I  Y  S  Y  H  I  K  G
AACTTCAACCAAAACAAAGATAAACACTGTTCCGCAAGCCCCTTTTTCAGACCGCTGGCT  2147
 T  S  T  K  T  K  I  N  T  V  P  Q  A  P  F  S  D  R  W  L
```

Fig.2B

```
AAAAGAAAATGCCGGTGCCGCTTCCGGTTTTCTCAGCCGTGCGGATGAAGCAGGAAAACT    2207
 K  E  N  A  G  A  A  S  G  F  L  S  R  A  D  E  A  G  K  L
GATATGGGAAAACGACCCCGATAAAAATTGGCGGGCTAACCGTATGGATGATATTCGCGG    2267
 I  W  E  N  D  P  D  K  N  W  R  A  N  R  M  D  D  I  R  G
CATCGTCCAAGGTGCGGTTAATCCTTTTTTAACGGGTTTTCAGGGATTGGGAGTTGGGGC    2327
 I  V  Q  G  A  V  N  P  F  L  T  G  F  Q  G  L  G  V  G  A
AATTACAGACAGTGCGGTAAGCCCGGTAACCTATGCGGCAGCACGGAAAACTTTACAGGG    2387
 I  T  D  S  A  V  S  P  V  T  Y  A  A  A  R  K  T  L  Q  G
TATTCACAATTTAGGAAATTTAAGTCCGGAAGCACAACTTGCCGCCGCGAGCCTATTACA    2447
 I  H  N  L  G  N  L  S  P  E  A  Q  L  A  A  A  S  L  L  Q
GGACAGTGCCTTTGCGGTAAAAGACGGCATCAATTCCGCCAGACAATGGGCTGATGCCCA    2507
 D  S  A  F  A  V  K  D  G  I  N  S  A  R  Q  W  A  D  A  H
```
PstI
```
TCCGAATATAACAGCAACAGCCCAAACTGCCCTTGCCGTAGCAGAGGCTGCAGGTACGGT    2567
 P  N  I  T  A  T  A  Q  T  A  L  A  V  A  E  A  A  G  T  V
TTGGGGAGGTAAAAAAGTAGAACTTAACCCGACCAAATGGGATTGGGTTAAAAATACCGG    2627
 W  G  G  K  K  V  E  L  N  P  T  K  W  D  W  V  K  N  T  G
CTATGAAAAACCTGCTGCCCGACCTATGCAGACTGTAGACGGGGAAATGGCCGGGAAAAA    2687
 Y  E  K  P  A  A  R  P  M  Q  T  V  D  G  E  M  A  G  K  N
TAAGCCACCGAAACCAAGTACGCAGCAACACTCTACACACTCTGATAACAATATCGGCTT    2747
 K  P  P  K  P  S  T  Q  Q  H  S  T  H  S  D  N  N  I  G  L
ACCTGCCCCATATGTTAAACCTGATACATCTATTTCTCCGACAGGAACAATTCAAGACCG    2807
 P  A  P  Y  V  K  P  D  T  S  I  S  P  T  G  T  I  Q  D  R
CATCAGATGGACAAAATCCAAGTTTCCTACTGAGAAATCTTTAAATGGACATTTCAAAGC    2867
 I  R  W  T  K  S  K  F  P  T  E  K  S  L  N  G  H  F  K  A
TCATGGAAAAGAATTTGGCGATATAACCATTGAAGACTACCAAAAAATGGCGTCTGATTT    2927
 H  G  K  E  F  G  D  I  T  I  E  D  Y  Q  K  M  A  S  D  L
GTTATCAAAACAGACATCGGACAAGATATTAGGTTATCAGACGGAACATAGACGAGTGCG    2987
 L  S  K  Q  T  S  D  K  I  L  G  Y  Q  T  E  H  R  R  V  R
CTATGATATCAATAACAATATCTATGTTTTGGCCAATCCAAAAACATTCAAAATCAAAAC    3047
 Y  D  I  N  N  N  I  Y  V  L  A  N  P  K  T  F  K  I  K  T
```
Eco RI
```
AATGTTTAAACCAAACTTAGGAAAGGAGTATTATGATGGAGAATTCAAAAAAGACATGGG    3107
 M  F  K  P  N  L  G  K  E  Y  Y  D  G  E  F  K  K  D  M  G
AAATTGACGGAGAAATATGGCTACATTGTCCTGTTTGCGGAACTGAAGTTATGGACTATG    3167
 N  *
ATATCTGTGACGTTTGTCAGTGGCAAAATACAGGAGAAACTAATATAGATGGTGGTCCTA    3227
```
HindIII
```
ATGAAATGACACTTGCGGAGGCGAAAGAAGCTTACGCAAAAGGCTTACCAATCAGATAAA    3287
```

Fig.2C

SEQUENCE LISTING

<160> NUMBER OF SEQ ID NOS: 7

<210> SEQ ID NO 1
<211> LENGTH: 3287
<212> TYPE: DNA
<213> ORGANISM: Neisseria gonorhoeae
<220> FEATURE:
<221> NAME/KEY: CDS
<222> LOCATION: (136)..(447)
<220> FEATURE:
<221> NAME/KEY: CDS
<222> LOCATION: (583)..(1542)
<220> FEATURE:
<221> NAME/KEY: CDS
<222> LOCATION: (1585)..(3111)

<400> SEQUENCE: 1

```
cggcgcaaac ggcggacgct gctgttagcc ccgcttgaaa caaatgccgt ctgaacgcca      60
cttcagacgg cattttttata ataaggcgct gtcctagata actagggaaa ttcaaattaa     120
gttagaatta tccct atg aga aaa agc cgt cta agc cgg tat aaa caa aat     171
              Met Arg Lys Ser Arg Leu Ser Arg Tyr Lys Gln Asn
                1               5                   10 aaa ctc att gaa ctg ttt gtc gca ggc gta act gca aga aca gca gca     219
Lys Leu Ile Glu Leu Phe Val Ala Gly Val Thr Ala Arg Thr Ala Ala
         15                  20                  25 gag cct gac agc att gtt tat acg gat tgt tat cgt cgc tat gat gta     267
Glu Pro Asp Ser Ile Val Tyr Thr Asp Cys Tyr Arg Arg Tyr Asp Val
     30                  35                  40 ttg gat gcg ggc gaa ttt agc cat ttc cgt atc aat cac agc aca cat     315
Leu Asp Ala Gly Glu Phe Ser His Phe Arg Ile Asn His Ser Thr His
45                  50                  55                  60 ttt gcc gaa cga caa aac cat att aat gga att ggg aac ttt tgg aac     363
Phe Ala Glu Arg Gln Asn His Ile Asn Gly Ile Gly Asn Phe Trp Asn
                 65                  70                  75 cgg gca aaa cgt cat tta cgc aag ttt gac ggc att ccc aaa gag cat     411
Arg Ala Lys Arg His Leu Arg Lys Phe Asp Gly Ile Pro Lys Glu His
             80                  85                  90 ttt gag ccg tat tta aag gag tgc gaa cgg cgt ttt taacaacagt          457
Phe Glu Pro Tyr Leu Lys Glu Cys Glu Arg Arg Phe
             95                 100 gagataaaag ttcttgttcc attttaaaac aattagtaaa atcgagttta tcctagttgt     517
ccaggacggc ccctaattta tttacaattt tgatacaatt tgttttttcat caaaggagaa     577 aatct atg cgg gca cgg ctg ctg ata cct att ctt ttt tcg gtt ttt att     627
      Met Arg Ala Arg Leu Leu Ile Pro Ile Leu Phe Ser Val Phe Ile
      105                 110                 115
```

```
                                                            -continued
tta tcc gcc tgc ggg aca ctg aca ggt att cca tcg cat ggc gga ggc    675
Leu Ser Ala Cys Gly Thr Leu Thr Gly Ile Pro Ser His Gly Gly Gly
120             125                 130                 135 aaa cgc ttc gcg gtc gaa caa gaa ctt gtg gcc gct tct gcc aga gct    723
Lys Arg Phe Ala Val Glu Gln Glu Leu Val Ala Ala Ser Ala Arg Ala
            140                 145                 150 gcc gtt aaa gac atg gat tta cag gca tta cac gga cga aaa gtt gca    771
Ala Val Lys Asp Met Asp Leu Gln Ala Leu His Gly Arg Lys Val Ala
        155                 160                 165 ttg tac att gca act atg ggc gac caa ggt tca ggc agt ttg aca ggg    819
Leu Tyr Ile Ala Thr Met Gly Asp Gln Gly Ser Gly Ser Leu Thr Gly
    170                 175                 180 ggt cgc tac tcc att gat gca ctg att cgc ggc gaa tac ata aac agc    867
Gly Arg Tyr Ser Ile Asp Ala Leu Ile Arg Gly Glu Tyr Ile Asn Ser
185                 190                 195 cct gcc gtc cgc acc gat tac acc tat ccg cgt tac gaa acc acc gct    915
Pro Ala Val Arg Thr Asp Tyr Thr Tyr Pro Arg Tyr Glu Thr Thr Ala
200                 205                 210                 215 gaa aca aca tca ggc ggt ttg acg ggt tta acc act tct tta tct aca    963
Glu Thr Thr Ser Gly Gly Leu Thr Gly Leu Thr Thr Ser Leu Ser Thr
            220                 225                 230 ctt aat gcc cct gca ctc tcg cgc acc caa tca gac ggt agc gga agt    1011
Leu Asn Ala Pro Ala Leu Ser Arg Thr Gln Ser Asp Gly Ser Gly Ser
        235                 240                 245 agg agc agt ctg ggc tta aat att ggc ggg atg ggg gat tat cga aat    1059
Arg Ser Ser Leu Gly Leu Asn Ile Gly Gly Met Gly Asp Tyr Arg Asn
    250                 255                 260 gaa acc ttg acg acc aac ccg cgc gac act gcc ttt ctt tcc cac ttg    1107
Glu Thr Leu Thr Thr Asn Pro Arg Asp Thr Ala Phe Leu Ser His Leu
265                 270                 275 gta cag acc gta ttt ttc ctg cgc ggc ata gac gtt gtt tct cct gcc    1155
Val Gln Thr Val Phe Phe Leu Arg Gly Ile Asp Val Val Ser Pro Ala
280                 285                 290                 295 aat gcc gat aca gat gtg ttt att aac atc gac gta ttc gga acg ata    1203
Asn Ala Asp Thr Asp Val Phe Ile Asn Ile Asp Val Phe Gly Thr Ile
            300                 305                 310 cgc aac aga acc gaa atg cac cta tac aat gcc gaa aca ctg aaa gcc    1251
Arg Asn Arg Thr Glu Met His Leu Tyr Asn Ala Glu Thr Leu Lys Ala
        315                 320                 325 caa aca aaa ctg gaa tat ttc gca gta gac aga acc aat aaa aaa ttg    1299
Gln Thr Lys Leu Glu Tyr Phe Ala Val Asp Arg Thr Asn Lys Lys Leu
    330                 335                 340 ctc atc aaa ccc aaa acc aat gcg ttt gaa gct gcc tat aaa gaa aat    1347
Leu Ile Lys Pro Lys Thr Asn Ala Phe Glu Ala Ala Tyr Lys Glu Asn
345                 350                 355 tac gca ttg tgg atg ggg ccg tat aaa gta agc aaa gga atc aaa ccg    1395
Tyr Ala Leu Trp Met Gly Pro Tyr Lys Val Ser Lys Gly Ile Lys Pro
360                 365                 370                 375 acg gaa gga tta atg gtc gat ttc tcc gat atc cgg cca tac ggc aat    1443
Thr Glu Gly Leu Met Val Asp Phe Ser Asp Ile Arg Pro Tyr Gly Asn
            380                 385                 390 cat acg ggt aac tcc gcc cca tcc gta gag gct gat aac agt cat gag    1491
His Thr Gly Asn Ser Ala Pro Ser Val Glu Ala Asp Asn Ser His Glu
        395                 400                 405 ggg tat gga tac agc gat gaa gca gtg cga caa cat aga caa ggg caa    1539
Gly Tyr Gly Tyr Ser Asp Glu Ala Val Arg Gln His Arg Gln Gly Gln
    410                 415                 420 cct tgattcacac tgccataacc gcttgctgcc aaggaaaaca aa atg aat ttg    1593
Pro                                                Met Asn Leu
                                                   425
```

```
cct att caa aaa ttc atg atg ctg ttt gca gcg gca ata tcg ttg ctg    1641
Pro Ile Gln Lys Phe Met Met Leu Phe Ala Ala Ala Ile Ser Leu Leu
        430                 435                 440 caa atc ccc att agt cat gcg aac ggt ttg gat gcc cgt ttg cgc gat    1689
Gln Ile Pro Ile Ser His Ala Asn Gly Leu Asp Ala Arg Leu Arg Asp
        445                 450                 455 gat atg cag gca aaa cac tac gaa ccg ggt ggc aaa tac cat ctg ttc    1737
Asp Met Gln Ala Lys His Tyr Glu Pro Gly Gly Lys Tyr His Leu Phe
460                 465                 470                 475 ggt aat gct cgc ggc agt gtt aaa aat cgg gtt tgc gcc gtc caa aca    1785
Gly Asn Ala Arg Gly Ser Val Lys Asn Arg Val Cys Ala Val Gln Thr
                480                 485                 490 ttt gat gca act gcg gtc ggc ccc ata ctg cct att aca cac gaa cgg    1833
Phe Asp Ala Thr Ala Val Gly Pro Ile Leu Pro Ile Thr His Glu Arg
                495                 500                 505 aca ggg ttt gaa ggc att atc ggt tat gaa acc cat ttt tca gga cac    1881
Thr Gly Phe Glu Gly Ile Ile Gly Tyr Glu Thr His Phe Ser Gly His
        510                 515                 520 gga cac gaa gta cac agt ccg ttc gat aat cat gat tca aaa agc act    1929
Gly His Glu Val His Ser Pro Phe Asp Asn His Asp Ser Lys Ser Thr
525                 530                 535 tct gat ttc agc ggc ggc gta gac ggc ggt ttt acc gtt tac caa ctt    1977
Ser Asp Phe Ser Gly Gly Val Asp Gly Gly Phe Thr Val Tyr Gln Leu
540                 545                 550                 555 cat cgg aca ggg tcg gaa ata cat ccc gca gac gga tat gac ggg cct    2025
His Arg Thr Gly Ser Glu Ile His Pro Ala Asp Gly Tyr Asp Gly Pro
                560                 565                 570 caa ggc ggc ggt tat ccg gaa cca caa ggg gca agg gat ata tac agc    2073
Gln Gly Gly Gly Tyr Pro Glu Pro Gln Gly Ala Arg Asp Ile Tyr Ser
                575                 580                 585 tac cat atc aaa gga act tca acc aaa aca aag ata aac act gtt ccg    2121
Tyr His Ile Lys Gly Thr Ser Thr Lys Thr Lys Ile Asn Thr Val Pro
        590                 595                 600 caa gcc cct ttt tca gac cgc tgg cta aaa gaa aat gcc ggt gcc gct    2169
Gln Ala Pro Phe Ser Asp Arg Trp Leu Lys Glu Asn Ala Gly Ala Ala
        605                 610                 615 tcc ggt ttt ctc agc cgt gcg gat gaa gca gga aaa ctg ata tgg gaa    2217
Ser Gly Phe Leu Ser Arg Ala Asp Glu Ala Gly Lys Leu Ile Trp Glu
620                 625                 630                 635 aac gac ccc gat aaa aat tgg cgg gct aac cgt atg gat gat att cgc    2265
Asn Asp Pro Asp Lys Asn Trp Arg Ala Asn Arg Met Asp Asp Ile Arg
                640                 645                 650 ggc atc gtc caa ggt gcg gtt aat cct ttt tta acg ggt ttt cag gga    2313
Gly Ile Val Gln Gly Ala Val Asn Pro Phe Leu Thr Gly Phe Gln Gly
                655                 660                 665 ttg gga gtt ggg gca att aca gac agt gcg gta agc ccg gta acc tat    2361
Leu Gly Val Gly Ala Ile Thr Asp Ser Ala Val Ser Pro Val Thr Tyr
        670                 675                 680 gcg gca gca cgg aaa act tta cag ggt att cac aat tta gga aat tta    2409
Ala Ala Ala Arg Lys Thr Leu Gln Gly Ile His Asn Leu Gly Asn Leu
        685                 690                 695 agt ccg gaa gca caa ctt gcc gcc gcc agc cta tta cag gac agt gcc    2457
Ser Pro Glu Ala Gln Leu Ala Ala Ala Ser Leu Leu Gln Asp Ser Ala
700                 705                 710                 715 ttt gcg gta aaa gac ggc atc aat tcc gcc aga caa tgg gct gat gcc    2505
Phe Ala Val Lys Asp Gly Ile Asn Ser Ala Arg Gln Trp Ala Asp Ala
                720                 725                 730 cat ccg aat ata aca gca aca gcc caa act gcc ctt gcc gta gca gag    2553
His Pro Asn Ile Thr Ala Thr Ala Gln Thr Ala Leu Ala Val Ala Glu
        735                 740                 745
```

-continued

| | | | | | | | | | | | | | | | | |
|---|---|---|---|---|---|---|---|---|---|---|---|---|---|---|---|---|
| gct | gca | ggt | acg | gtt | tgg | gga | ggt | aaa | aaa | gta | gaa | ctt | aac | ccg | acc | 2601 |
| Ala | Ala | Gly | Thr | Val | Trp | Gly | Gly | Lys | Lys | Val | Glu | Leu | Asn | Pro | Thr | |
| | | 750 | | | | | 755 | | | | | 760 | | | | |

| aaa | tgg | gat | tgg | gtt | aaa | aat | acc | ggc | tat | gaa | aaa | cct | gct | gcc | cga | 2649 |
| Lys | Trp | Asp | Trp | Val | Lys | Asn | Thr | Gly | Tyr | Glu | Lys | Pro | Ala | Ala | Arg | |
| 765 | | | | | 770 | | | | | 775 | | | | | | |

| cct | atg | cag | act | gta | gac | ggg | gaa | atg | gcc | ggg | aaa | aat | aag | cca | ccg | 2697 |
| Pro | Met | Gln | Thr | Val | Asp | Gly | Glu | Met | Ala | Gly | Lys | Asn | Lys | Pro | Pro | |
| 780 | | | | | 785 | | | | | 790 | | | | | 795 | |

| aaa | cca | agt | acg | cag | caa | cac | tct | aca | cac | tct | gat | aac | aat | atc | ggc | 2745 |
| Lys | Pro | Ser | Thr | Gln | Gln | His | Ser | Thr | His | Ser | Asp | Asn | Asn | Ile | Gly | |
| | | | | 800 | | | | | 805 | | | | | 810 | | |

| tta | cct | gcc | cca | tat | gtt | aaa | cct | gat | aca | tct | att | tct | ccg | aca | gga | 2793 |
| Leu | Pro | Ala | Pro | Tyr | Val | Lys | Pro | Asp | Thr | Ser | Ile | Ser | Pro | Thr | Gly | |
| | | | | | 815 | | | | | 820 | | | | | 825 | |

| aca | att | caa | gac | cgc | atc | aga | tgg | aca | aaa | tcc | aag | ttt | cct | act | gag | 2841 |
| Thr | Ile | Gln | Asp | Arg | Ile | Arg | Trp | Thr | Lys | Ser | Lys | Phe | Pro | Thr | Glu | |
| | | | 830 | | | | | 835 | | | | | 840 | | | |

| aaa | tct | tta | aat | gga | cat | ttc | aaa | gct | cat | gga | aaa | gaa | ttt | ggc | gat | 2889 |
| Lys | Ser | Leu | Asn | Gly | His | Phe | Lys | Ala | His | Gly | Lys | Glu | Phe | Gly | Asp | |
| 845 | | | | | 850 | | | | | 855 | | | | | | |

| ata | acc | att | gaa | gac | tac | caa | aaa | atg | gcg | tct | gat | ttg | tta | tca | aaa | 2937 |
| Ile | Thr | Ile | Glu | Asp | Tyr | Gln | Lys | Met | Ala | Ser | Asp | Leu | Leu | Ser | Lys | |
| 860 | | | | | 865 | | | | | 870 | | | | | 875 | |

| cag | aca | tcg | gac | aag | ata | tta | ggt | tat | cag | acg | gaa | cat | aga | cga | gtg | 2985 |
| Gln | Thr | Ser | Asp | Lys | Ile | Leu | Gly | Tyr | Gln | Thr | Glu | His | Arg | Arg | Val | |
| | | | | 880 | | | | | 885 | | | | | 890 | | |

| cgc | tat | gat | atc | aat | aac | aat | atc | tat | gtt | ttg | gcc | aat | cca | aaa | aca | 3033 |
| Arg | Tyr | Asp | Ile | Asn | Asn | Asn | Ile | Tyr | Val | Leu | Ala | Asn | Pro | Lys | Thr | |
| | | | | 895 | | | | | 900 | | | | | 905 | | |

| ttc | aaa | atc | aaa | aca | atg | ttt | aaa | cca | aac | tta | gga | aag | gag | tat | tat | 3081 |
| Phe | Lys | Ile | Lys | Thr | Met | Phe | Lys | Pro | Asn | Leu | Gly | Lys | Glu | Tyr | Tyr | |
| | | | 910 | | | | | 915 | | | | | 920 | | | |

| gat | gga | gaa | ttc | aaa | aaa | gac | atg | gga | aat | tgacggagaa atatggctac | 3131 |
| Asp | Gly | Glu | Phe | Lys | Lys | Asp | Met | Gly | Asn | | |
| 925 | | | | | 930 | | | | | | | attgtcctgt tgcggaact gaagttatgg actatgatat ctgtgacgtt tgtcagtggc 3191 aaaatacagg agaaactaat atagatggtg gtcctaatga aatgacactt gcggaggcga 3251 aagaagctta cgcaaaaggc ttaccaatca gataaa 3287

<210> SEQ ID NO 2
<211> LENGTH: 1136
<212> TYPE: DNA
<213> ORGANISM: Neisseria gonorrhoeae
<220> FEATURE:
<221> NAME/KEY: CDS
<222> LOCATION: (135)..(1094)

<400> SEQUENCE: 2
aacaacagtg agataaaagt tcttgttcca ttttaaaaca attagtaaaa tcgagtttat    60
cctagttgtc caggacggcc cctaatttat ttacaatttt gatacaattt gttttcatc   120

| aaaggagaaa atct | atg | cgg | gca | cgg | ctg | ctg | ata | cct | att | ctt | ttt | tcg | 170 |
|---|---|---|---|---|---|---|---|---|---|---|---|---|---|
| | Met | Arg | Ala | Arg | Leu | Leu | Ile | Pro | Ile | Leu | Phe | Ser | |
| | 1 | | | | 5 | | | | | 10 | | | |

| gtt | ttt | att | tta | tcc | gcc | tgc | ggg | aca | ctg | aca | ggt | att | cca | tcg | cat | 218 |
| Val | Phe | Ile | Leu | Ser | Ala | Cys | Gly | Thr | Leu | Thr | Gly | Ile | Pro | Ser | His | |
| | 15 | | | | | 20 | | | | | 25 | | | | | |

| ggc | gga | ggc | aaa | cgc | ttc | gcg | gtc | gaa | caa | gaa | ctt | gtg | gcc | gct | tct | 266 |
| Gly | Gly | Gly | Lys | Arg | Phe | Ala | Val | Glu | Gln | Glu | Leu | Val | Ala | Ala | Ser | |
| 30 | | | | | 35 | | | | | 40 | | | | | | |

| | | |
|---|---|---|
| gcc aga gct gcc gtt aaa gac atg gat tta cag gca tta cac gga cga<br>Ala Arg Ala Ala Val Lys Asp Met Asp Leu Gln Ala Leu His Gly Arg<br>45                       50                    55                    60 | | 314 |
| aaa gtt gca ttg tac att gca act atg ggc gac caa ggt tca ggc agt<br>Lys Val Ala Leu Tyr Ile Ala Thr Met Gly Asp Gln Gly Ser Gly Ser<br>                 65                    70                    75 | | 362 |
| ttg aca ggg ggt cgc tac tcc att gat gca ctg att cgc ggc gaa tac<br>Leu Thr Gly Gly Arg Tyr Ser Ile Asp Ala Leu Ile Arg Gly Glu Tyr<br>            80                    85                    90 | | 410 |
| ata aac agc cct gcc gtc cgc acc gat tac acc tat ccg cgt tac gaa<br>Ile Asn Ser Pro Ala Val Arg Thr Asp Tyr Thr Tyr Pro Arg Tyr Glu<br>                95                   100               105 | | 458 |
| acc acc gct gaa aca aca tca ggc ggt ttg acg ggt tta acc act tct<br>Thr Thr Ala Glu Thr Thr Ser Gly Gly Leu Thr Gly Leu Thr Thr Ser<br>110                      115                  120 | | 506 |
| tta tct aca ctt aat gcc cct gca ctc tcg cgc acc caa tca gac ggt<br>Leu Ser Thr Leu Asn Ala Pro Ala Leu Ser Arg Thr Gln Ser Asp Gly<br>125                      130                  135               140 | | 554 |
| agc gga agt agg agc agt ctg ggc tta aat att ggc ggg atg ggg gat<br>Ser Gly Ser Arg Ser Ser Leu Gly Leu Asn Ile Gly Gly Met Gly Asp<br>                      145                  150               155 | | 602 |
| tat cga aat gaa acc ttg acg acc aac ccg cgc gac act gcc ttt ctt<br>Tyr Arg Asn Glu Thr Leu Thr Thr Asn Pro Arg Asp Thr Ala Phe Leu<br>                  160                  165               170 | | 650 |
| tcc cac ttg gta cag acc gta ttt ttc ctg cgc ggc ata gac gtt gtt<br>Ser His Leu Val Gln Thr Val Phe Phe Leu Arg Gly Ile Asp Val Val<br>175                      180                  185 | | 698 |
| tct cct gcc aat gcc gat aca gat gtg ttt att aac atc gac gta ttc<br>Ser Pro Ala Asn Ala Asp Thr Asp Val Phe Ile Asn Ile Asp Val Phe<br>            190                  195               200 | | 746 |
| gga acg ata cgc aac aga acc gaa atg cac cta tac aat gcc gaa aca<br>Gly Thr Ile Arg Asn Arg Thr Glu Met His Leu Tyr Asn Ala Glu Thr<br>205                      210                  215               220 | | 794 |
| ctg aaa gcc caa aca aaa ctg gaa tat ttc gca gta gac aga acc aat<br>Leu Lys Ala Gln Thr Lys Leu Glu Tyr Phe Ala Val Asp Arg Thr Asn<br>                      225                  230               235 | | 842 |
| aaa aaa ttg ctc atc aaa ccc aaa acc aat gcg ttt gaa gct gcc tat<br>Lys Lys Leu Leu Ile Lys Pro Lys Thr Asn Ala Phe Glu Ala Ala Tyr<br>            240                    245               250 | | 890 |
| aaa gaa aat tac gca ttg tgg atg ggg ccg tat aaa gta agc aaa gga<br>Lys Glu Asn Tyr Ala Leu Trp Met Gly Pro Tyr Lys Val Ser Lys Gly<br>255                      260                  265 | | 938 |
| atc aaa ccg acg gaa gga tta atg gtc gat ttc tcc gat atc cgg cca<br>Ile Lys Pro Thr Glu Gly Leu Met Val Asp Phe Ser Asp Ile Arg Pro<br>            270                    275               280 | | 986 |
| tac ggc aat cat acg ggt aac tcc gcc cca tcc gta gag gct gat aac<br>Tyr Gly Asn His Thr Gly Asn Ser Ala Pro Ser Val Glu Ala Asp Asn<br>285                      290                  295               300 | | 1034 |
| agt cat gag ggg tat gga tac agc gat gaa gca gtg cga caa cat aga<br>Ser His Glu Gly Tyr Gly Tyr Ser Asp Glu Ala Val Arg Gln His Arg<br>                      305                  310               315 | | 1082 |
| caa ggg caa cct tgattcacac tgccataacc gcttgctgcc aaggaaaaca aa<br>Gln Gly Gln Pro<br>                 320 | | 1136 |

<210> SEQ ID NO 3
<211> LENGTH: 582
<212> TYPE: DNA
<213> ORGANISM: Neisseria gonorrhoeae
<220> FEATURE:
<221> NAME/KEY: CDS

```
<222> LOCATION: (136)..(447)

<400> SEQUENCE: 3
cggcgcaaac ggcggacgct gctgttagcc ccgcttgaaa caaatgccgt ctgaacgcca      60
cttcagacgg cattttata ataaggcgct gtcctagata actagggaaa ttcaaattaa     120
gttagaatta tccct atg aga aaa agc cgt cta agc cgg tat aaa caa aat     171
              Met Arg Lys Ser Arg Leu Ser Arg Tyr Lys Gln Asn
                1               5                  10 aaa ctc att gaa ctg ttt gtc gca ggc gta act gca aga aca gca gca     219
Lys Leu Ile Glu Leu Phe Val Ala Gly Val Thr Ala Arg Thr Ala Ala
         15                  20                  25 gag cct gac agc att gtt tat acg gat tgt tat cgt cgc tat gat gta     267
Glu Pro Asp Ser Ile Val Tyr Thr Asp Cys Tyr Arg Arg Tyr Asp Val
     30                  35                  40 ttg gat gcg ggc gaa ttt agc cat ttc cgt atc aat cac agc aca cat     315
Leu Asp Ala Gly Glu Phe Ser His Phe Arg Ile Asn His Ser Thr His
 45                  50                  55                  60 ttt gcc gaa cga caa aac cat att aat gga att ggg aac ttt tgg aac     363
Phe Ala Glu Arg Gln Asn His Ile Asn Gly Ile Gly Asn Phe Trp Asn
                 65                  70                  75 cgg gca aaa cgt cat tta cgc aag ttt gac ggc att ccc aaa gag cat     411
Arg Ala Lys Arg His Leu Arg Lys Phe Asp Gly Ile Pro Lys Glu His
             80                  85                  90 ttt gag ccg tat tta aag gag tgc gaa cgg cgt ttt taacaacagt           457
Phe Glu Pro Tyr Leu Lys Glu Cys Glu Arg Arg Phe
         95                 100 gagataaaag ttcttgttcc attttaaaac aattagtaaa atcgagttta tcctagttgt     517
ccaggacggc ccctaattta tttacaattt tgatacaatt tgttttcat caaaggagaa      577 aatct                                                                  582

<210> SEQ ID NO 4
<211> LENGTH: 1744
<212> TYPE: DNA
<213> ORGANISM: Neisseria gonorrhoeae
<220> FEATURE:
<221> NAME/KEY: CDS
<222> LOCATION: (42)..(1568)

<400> SEQUENCE: 4
gattcacact gccataaccg cttgctgcca aggaaaacaa a atg aat ttg cct att      56
                                              Met Asn Leu Pro Ile
                                                1               5 caa aaa ttc atg atg ctg ttt gca gcg gca ata tcg ttg ctg caa atc     104
Gln Lys Phe Met Met Leu Phe Ala Ala Ala Ile Ser Leu Leu Gln Ile
             10                  15                  20 ccc att agt cat gcg aac ggt ttg gat gcc cgt ttg cgc gat gat atg     152
Pro Ile Ser His Ala Asn Gly Leu Asp Ala Arg Leu Arg Asp Asp Met
             25                  30                  35 cag gca aaa cac tac gaa ccg ggt ggc aaa tac cat ctg ttc ggt aat     200
Gln Ala Lys His Tyr Glu Pro Gly Gly Lys Tyr His Leu Phe Gly Asn
     40                  45                  50 gct cgc ggc agt gtt aaa aat cgg gtt tgc gcc gtc caa aca ttt gat     248
Ala Arg Gly Ser Val Lys Asn Arg Val Cys Ala Val Gln Thr Phe Asp
 55                  60                  65 gca act gcg gtc ggc ccc ata ctg cct att aca cac gaa cgg aca ggg     296
Ala Thr Ala Val Gly Pro Ile Leu Pro Ile Thr His Glu Arg Thr Gly
 70                  75                  80                  85 ttt gaa ggc att atc ggt tat gaa acc cat ttt tca gga cac gga cac     344
Phe Glu Gly Ile Ile Gly Tyr Glu Thr His Phe Ser Gly His Gly His
                 90                  95                 100
```

```
gaa gta cac agt ccg ttc gat aat cat gat tca aaa agc act tct gat    392
Glu Val His Ser Pro Phe Asp Asn His Asp Ser Lys Ser Thr Ser Asp
        105                 110                 115 ttc agc ggc ggc gta gac ggc ggt ttt acc gtt tac caa ctt cat cgg    440
Phe Ser Gly Gly Val Asp Gly Gly Phe Thr Val Tyr Gln Leu His Arg
        120                 125                 130 aca ggg tcg gaa ata cat ccc gca gac gga tat gac ggg cct caa ggc    488
Thr Gly Ser Glu Ile His Pro Ala Asp Gly Tyr Asp Gly Pro Gln Gly
        135                 140                 145 ggc ggt tat ccg gaa cca caa ggg gca agg gat ata tac agc tac cat    536
Gly Gly Tyr Pro Glu Pro Gln Gly Ala Arg Asp Ile Tyr Ser Tyr His
150                 155                 160                 165 atc aaa gga act tca acc aaa aca aag ata aac act gtt ccg caa gcc    584
Ile Lys Gly Thr Ser Thr Lys Thr Lys Ile Asn Thr Val Pro Gln Ala
        170                 175                 180 cct ttt tca gac cgc tgg cta aaa gaa aat gcc ggt gcc gct tcc ggt    632
Pro Phe Ser Asp Arg Trp Leu Lys Glu Asn Ala Gly Ala Ala Ser Gly
        185                 190                 195 ttt ctc agc cgt gcg gat gaa gca gga aaa ctg ata tgg gaa aac gac    680
Phe Leu Ser Arg Ala Asp Glu Ala Gly Lys Leu Ile Trp Glu Asn Asp
        200                 205                 210 ccc gat aaa aat tgg cgg gct aac cgt atg gat gat att cgc ggc atc    728
Pro Asp Lys Asn Trp Arg Ala Asn Arg Met Asp Asp Ile Arg Gly Ile
        215                 220                 225 gtc caa ggt gcg gtt aat cct ttt tta acg ggt ttt cag gga ttg gga    776
Val Gln Gly Ala Val Asn Pro Phe Leu Thr Gly Phe Gln Gly Leu Gly
230                 235                 240                 245 gtt ggg gca att aca gac agt gcg gta agc ccg gta acc tat gcg gca    824
Val Gly Ala Ile Thr Asp Ser Ala Val Ser Pro Val Thr Tyr Ala Ala
        250                 255                 260 gca cgg aaa act tta cag ggt att cac aat tta gga aat tta agt ccg    872
Ala Arg Lys Thr Leu Gln Gly Ile His Asn Leu Gly Asn Leu Ser Pro
        265                 270                 275 gaa gca caa ctt gcc gcc gcg agc cta tta cag gac agt gcc ttt gcg    920
Glu Ala Gln Leu Ala Ala Ala Ser Leu Leu Gln Asp Ser Ala Phe Ala
        280                 285                 290 gta aaa gac ggc atc aat tcc gcc aga caa tgg gct gat gcc cat ccg    968
Val Lys Asp Gly Ile Asn Ser Ala Arg Gln Trp Ala Asp Ala His Pro
        295                 300                 305 aat ata aca gca aca gcc caa act gcc ctt gcc gta gca gag gct gca   1016
Asn Ile Thr Ala Thr Ala Gln Thr Ala Leu Ala Val Ala Glu Ala Ala
310                 315                 320                 325 ggt acg gtt tgg gga ggt aaa aaa gta gaa ctt aac ccg acc aaa tgg   1064
Gly Thr Val Trp Gly Gly Lys Lys Val Glu Leu Asn Pro Thr Lys Trp
        330                 335                 340 gat tgg gtt aaa aat acc ggc tat gaa aaa cct gct gcc cga cct atg   1112
Asp Trp Val Lys Asn Thr Gly Tyr Glu Lys Pro Ala Ala Arg Pro Met
        345                 350                 355 cag act gta gac ggg gaa atg gcc ggg aaa aat aag cca ccg aaa cca   1160
Gln Thr Val Asp Gly Glu Met Ala Gly Lys Asn Lys Pro Pro Lys Pro
        360                 365                 370 agt acg cag caa cac tct aca cac tct gat aac aat atc ggc tta cct   1208
Ser Thr Gln Gln His Ser Thr His Ser Asp Asn Asn Ile Gly Leu Pro
375                 380                 385 gcc cca tat gtt aaa cct gat aca tct att tct ccg aca gga aca att   1256
Ala Pro Tyr Val Lys Pro Asp Thr Ser Ile Ser Pro Thr Gly Thr Ile
390                 395                 400                 405 caa gac cgc atc aga tgg aca aaa tcc aag ttt cct act gag aaa tct   1304
Gln Asp Arg Ile Arg Trp Thr Lys Ser Lys Phe Pro Thr Glu Lys Ser
        410                 415                 420
```

-continued

```
tta aat gga cat ttc aaa gct cat gga aaa gaa ttt ggc gat ata acc    1352
Leu Asn Gly His Phe Lys Ala His Gly Lys Glu Phe Gly Asp Ile Thr
            425                 430                 435 att gaa gac tac caa aaa atg gcg tct gat ttg tta tca aaa cag aca    1400
Ile Glu Asp Tyr Gln Lys Met Ala Ser Asp Leu Leu Ser Lys Gln Thr
        440                 445                 450 tcg gac aag ata tta ggt tat cag acg gaa cat aga cga gtg cgc tat    1448
Ser Asp Lys Ile Leu Gly Tyr Gln Thr Glu His Arg Arg Val Arg Tyr
    455                 460                 465 gat atc aat aac aat atc tat gtt ttg gcc aat cca aaa aca ttc aaa    1496
Asp Ile Asn Asn Asn Ile Tyr Val Leu Ala Asn Pro Lys Thr Phe Lys
470                 475                 480                 485 atc aaa aca atg ttt aaa cca aac tta gga aag gag tat tat gat gga    1544
Ile Lys Thr Met Phe Lys Pro Asn Leu Gly Lys Glu Tyr Tyr Asp Gly
                490                 495                 500 gaa ttc aaa aaa gac atg gga aat tgacggagaa atatggctac attgtcctgt    1598
Glu Phe Lys Lys Asp Met Gly Asn
                505 ttgcggaact gaagttatgg actatgatat ctgtgacgtt tgtcagtggc aaaatacagg    1658 agaaactaat atagatggtg gtcctaatga aatgacactt gcggaggcga agaagctta     1718 cgcaaaaggc ttaccaatca gataaa                                         1744

<210> SEQ ID NO 5
<211> LENGTH: 320
<212> TYPE: PRT
<213> ORGANISM: Neisseria gonorrhoeae
<220> FEATURE:
<221> NAME/KEY: misc_feature
<223> OTHER INFORMATION: OrfA protein encoded by SEQ ID NO: 2

<400> SEQUENCE: 5

Met Arg Ala Arg Leu Leu Ile Pro Ile Leu Phe Ser Val Phe Ile Leu
1               5                   10                  15

Ser Ala Cys Gly Thr Leu Thr Gly Ile Pro Ser His Gly Gly Gly Lys
            20                  25                  30

Arg Phe Ala Val Glu Gln Glu Leu Val Ala Ala Ser Ala Arg Ala Ala
        35                  40                  45

Val Lys Asp Met Asp Leu Gln Ala Leu His Gly Arg Lys Val Ala Leu
    50                  55                  60

Tyr Ile Ala Thr Met Gly Asp Gln Gly Ser Gly Ser Leu Thr Gly Gly
65                  70                  75                  80

Arg Tyr Ser Ile Asp Ala Leu Ile Arg Gly Glu Tyr Ile Asn Ser Pro
                85                  90                  95

Ala Val Arg Thr Asp Tyr Thr Tyr Pro Arg Tyr Glu Thr Thr Ala Glu
            100                 105                 110

Thr Thr Ser Gly Gly Leu Thr Gly Leu Thr Thr Ser Leu Ser Thr Leu
        115                 120                 125

Asn Ala Pro Ala Leu Ser Arg Thr Gln Ser Asp Gly Ser Gly Ser Arg
    130                 135                 140

Ser Ser Leu Gly Leu Asn Ile Gly Gly Met Gly Asp Tyr Arg Asn Glu
145                 150                 155                 160

Thr Leu Thr Thr Asn Pro Arg Asp Thr Ala Phe Leu Ser His Leu Val
                165                 170                 175

Gln Thr Val Phe Phe Leu Arg Gly Ile Asp Val Val Ser Pro Ala Asn
            180                 185                 190

Ala Asp Thr Asp Val Phe Ile Asn Ile Asp Val Phe Gly Thr Ile Arg
        195                 200                 205
```

```
Asn Arg Thr Glu Met His Leu Tyr Asn Ala Glu Thr Leu Lys Ala Gln
        210                 215                 220

Thr Lys Leu Glu Tyr Phe Ala Val Asp Arg Thr Asn Lys Lys Leu Leu
225                 230                 235                 240

Ile Lys Pro Lys Thr Asn Ala Phe Glu Ala Ala Tyr Lys Glu Asn Tyr
                245                 250                 255

Ala Leu Trp Met Gly Pro Tyr Lys Val Ser Lys Gly Ile Lys Pro Thr
            260                 265                 270

Glu Gly Leu Met Val Asp Phe Ser Asp Ile Arg Pro Tyr Gly Asn His
        275                 280                 285

Thr Gly Asn Ser Ala Pro Ser Val Glu Ala Asp Asn Ser His Glu Gly
        290                 295                 300

Tyr Gly Tyr Ser Asp Glu Ala Val Arg Gln His Arg Gln Gly Gln Pro
305                 310                 315                 320

<210> SEQ ID NO 6
<211> LENGTH: 104
<212> TYPE: PRT
<213> ORGANISM: Neisseria gonorrhoeae
<220> FEATURE:
<221> NAME/KEY: misc_feature
<223> OTHER INFORMATION: Orfl protein encoded by SEQ ID NO: 3

<400> SEQUENCE: 6

Met Arg Lys Ser Arg Leu Ser Arg Tyr Lys Gln Asn Lys Leu Ile Glu
1               5                   10                  15

Leu Phe Val Ala Gly Val Thr Ala Arg Thr Ala Ala Glu Pro Asp Ser
            20                  25                  30

Ile Val Tyr Thr Asp Cys Tyr Arg Arg Tyr Asp Val Leu Asp Ala Gly
        35                  40                  45

Glu Phe Ser His Phe Arg Ile Asn His Ser Thr His Phe Ala Glu Arg
    50                  55                  60

Gln Asn His Ile Asn Gly Ile Gly Asn Phe Trp Asn Arg Ala Lys Arg
65                  70                  75                  80

His Leu Arg Lys Phe Asp Gly Ile Pro Lys Glu His Phe Glu Pro Tyr
                85                  90                  95

Leu Lys Glu Cys Glu Arg Arg Phe
            100

<210> SEQ ID NO 7
<211> LENGTH: 509
<212> TYPE: PRT
<213> ORGANISM: Neisseria gonorrhoeae
<220> FEATURE:
<221> NAME/KEY: misc_feature
<223> OTHER INFORMATION: OrfB protein encoded by SEQ ID NO: 4

<400> SEQUENCE: 7

Met Asn Leu Pro Ile Gln Lys Phe Met Met Leu Phe Ala Ala Ala Ile
1               5                   10                  15

Ser Leu Leu Gln Ile Pro Ile Ser His Ala Asn Gly Leu Asp Ala Arg
            20                  25                  30

Leu Arg Asp Asp Met Gln Ala Lys His Tyr Glu Pro Gly Gly Lys Tyr
        35                  40                  45

His Leu Phe Gly Asn Ala Arg Gly Ser Val Lys Asn Arg Val Cys Ala
    50                  55                  60

Val Gln Thr Phe Asp Ala Thr Ala Val Gly Pro Ile Leu Pro Ile Thr
65                  70                  75                  80
```

His Glu Arg Thr Gly Phe Gly Ile Ile Gly Tyr Glu Thr His Phe
                85                  90                  95

Ser Gly His Gly His Glu Val His Ser Pro Phe Asp Asn His Asp Ser
            100                 105                 110

Lys Ser Thr Ser Asp Phe Ser Gly Gly Val Asp Gly Gly Phe Thr Val
            115                 120                 125

Tyr Gln Leu His Arg Thr Gly Ser Glu Ile His Pro Ala Asp Gly Tyr
            130                 135                 140

Asp Gly Pro Gln Gly Gly Tyr Pro Glu Pro Gln Gly Ala Arg Asp
145                 150                 155                 160

Ile Tyr Ser Tyr His Ile Lys Gly Thr Ser Thr Lys Thr Lys Ile Asn
                165                 170                 175

Thr Val Pro Gln Ala Pro Phe Ser Asp Arg Trp Leu Lys Glu Asn Ala
            180                 185                 190

Gly Ala Ala Ser Gly Phe Leu Ser Arg Ala Asp Glu Ala Gly Lys Leu
            195                 200                 205

Ile Trp Glu Asn Asp Pro Asp Lys Asn Trp Arg Ala Asn Arg Met Asp
            210                 215                 220

Asp Ile Arg Gly Ile Val Gln Gly Ala Val Asn Pro Phe Leu Thr Gly
225                 230                 235                 240

Phe Gln Gly Leu Gly Val Gly Ala Ile Thr Asp Ser Ala Val Ser Pro
                245                 250                 255

Val Thr Tyr Ala Ala Ala Arg Lys Thr Leu Gln Gly Ile His Asn Leu
                260                 265                 270

Gly Asn Leu Ser Pro Glu Ala Gln Leu Ala Ala Ala Ser Leu Leu Gln
            275                 280                 285

Asp Ser Ala Phe Ala Val Lys Asp Gly Ile Asn Ser Ala Arg Gln Trp
            290                 295                 300

Ala Asp Ala His Pro Asn Ile Thr Ala Thr Ala Gln Thr Ala Leu Ala
305                 310                 315                 320

Val Ala Glu Ala Ala Gly Thr Val Trp Gly Gly Lys Lys Val Glu Leu
                325                 330                 335

Asn Pro Thr Lys Trp Asp Trp Val Lys Asn Thr Gly Tyr Glu Lys Pro
            340                 345                 350

Ala Ala Arg Pro Met Gln Thr Val Asp Gly Glu Met Ala Gly Lys Asn
            355                 360                 365

Lys Pro Pro Lys Pro Ser Thr Gln Gln His Ser Thr His Ser Asp Asn
            370                 375                 380

Asn Ile Gly Leu Pro Ala Pro Tyr Val Lys Pro Asp Thr Ser Ile Ser
385                 390                 395                 400

Pro Thr Gly Thr Ile Gln Asp Arg Ile Arg Trp Thr Lys Ser Lys Phe
                405                 410                 415

Pro Thr Glu Lys Ser Leu Asn Gly His Phe Lys Ala His Gly Lys Glu
            420                 425                 430

Phe Gly Asp Ile Thr Ile Glu Asp Tyr Gln Lys Met Ala Ser Asp Leu
            435                 440                 445

Leu Ser Lys Gln Thr Ser Asp Lys Ile Leu Gly Tyr Gln Thr Glu His
            450                 455                 460

Arg Arg Val Arg Tyr Asp Ile Asn Asn Asn Ile Tyr Val Leu Ala Asn
465                 470                 475                 480

Pro Lys Thr Phe Lys Ile Lys Thr Met Phe Lys Pro Asn Leu Gly Lys
                485                 490                 495

```
Glu Tyr Tyr Asp Gly Glu Phe Lys Lys Asp Met Gly Asn
            500                 505
```

NUCLEIC ACID MOLECULES ENCODING PROTEINS WHICH IMPART THE ADHESION OF *NEISSERIA* CELLS TO HUMAN CELLS

This application is a Divisional of U.S. patent application Ser. No. 10/617,835 filed on Jul. 14, 2003, now abandoned, which is a Divisional of U.S. patent application Ser. No. 09/043,302, filed on Jun. 8, 1998, now U.S. Pat. No. 6,617, 128, both of which priority is claimed under 35 U.S.C. §120, which is the national phase of PCT International Application No. PCT/EP96/04092 filed on Sep. 18, 1996 under 35 U.S.C. §371, which claims priority to Application No. 19534579.7 filed in Germany on Sep. 18, 1995. The entire contents of each of the above-identified applications are hereby incorporated by reference. This application also claims priority of Application No. 19534579.7 filed in Germany under 35 U.S.C. §119.

The present invention relates to nucleic acid molecules from bacteria of the genus *Neisseria* encoding proteins mediating the adhesion of *Neisseria* cells to human cells. Furthermore, the present invention relates to the proteins encoded by these nucleic acid molecules and to antibodies directed against them. The present invention further relates to pharmaceutical compositions, vaccines and diagnostic compositions containing said nucleic acid molecules, proteins and/or antibodies.

To the genus *Neisseria* (gram-negative cocci) belong a number of bacterial species which, being saprophytes, populate the upper human respiratory tract. Apart from commensal species (e.g.: *N. sicca*) and opportunistically pathogenic species (e.g.: *N. lactamica*), two *Neisseria* species are known which clearly possess human-pathogenic properties. One of the species is *N. gonorrhoeae*, the pathogen of the venereal disease gonorrhea, which exclusively occurs in humans, and *N. meningitidis*, the pathogen of the bacterial epidemic meningitis. In both cases the etiology, that is the causal connection between the development of the clinical picture and the population by bacteria from said species has meanwhile been substantiated.

The purulent meningitis (Meningitidis cerebrospinalis epidemica) caused by *N. meningitidis* ("meningococcus"), which usually is epidemical, is a systemic invasive infection of the human meninx and spinal meninx. Occasionally, hemorrhagic exanthema at the trunk or concomitant diseases caused by Herpes simplex can be observed in addition. The pathogen can appear in the form of several serotypes, which are distinguishable by means of agglutination assays with immune sera. The main groups differ remarkably, and their prevalence differs with regard to when and where they appear. Meningococcus meningitidis has up to now occurred in large numbers every 8 to 12 years with the increased prevalence lasting between 4 to 6 years. While serovar B meningococci brought on 50% to 55% of the recent diseases to the civilian population as well as to the military personnel in the United States, most epidemic diseases in the United States during the first half of the century were caused by serovar A meningococci.

The clinical picture caused by *N. gonorrhoeae* usually is an infection localized to the mucous membranes, in most cases of the urogenital tract (gonorrhea), more rarely of the conjunctiva (conjunctivis gonorrhoeae, gonoblennorrhoe), which is acquired by new born children perinatally, by adults usually unilaterally by smear infection. In very rare cases bacteremia and sepsis occur after hematogenous dissemination. As a consequence, exanthema with hemorrhagic pustules, diseases from the rheumatic Formenkreis, arthritis gonorrhoica and/or endocarditis can occur.

Usually, the diseases caused by *N. gonorrhoeae* and *N. meningitidis* are treated with antibiotics. More and more, however, the bacteria are becoming resistant to single or groups of the antibiotics used so that the therapy method that has nearly exclusively been used up to now will most likely not be successful in the long run. Therefore, it is desirable and urgent that alternative therapy methods, preferably preventive ones, be developed.

*Neisseria gonorrhoeae* and *N. meningitidis* exclusively occur in humans. They have adapted to the host organism and show a number of properties that are able to make the defense mechanisms of the host ineffective. Therefore, up to now there is no vaccine available that prevents gonorrhea. This is to a limited extent also true for meningococcus meningitidis. Even though the disease has recently been caused mainly by bacteria of the same serovar, group B, no effective vaccine against meningococci of group B has existed up to now. Vaccines against other serovars only offer partial protection and are not unproblematic from an immunological point of view. The reason for the failure of the immune defense is, inter alia, the antigen variation of the pathogens, which in the case of the pathogenic *Neisseria* is particularly developed. However, a limitation of the free development of the antigen variation seems to be necessary where the functional region has to be sterically maintained in order to guarantee the interaction with conserved and constant structures of the host receptors. This requirement especially applies to the adhesins that serve for adhering to the host cell. Only if the functional region that is involved in the physical interaction is kept constant, the interaction with the receptor of the host cell is possible. This region should be excluded from antigen variation to a large extent and is therefore a suitable starting-point for the development of a new therapy method.

The initial phase of infections usually is the stable adhesion of the pathogens to the host tissue. By interactions between structures of the cell surface of the pathogens and the cell surface of the host cell a mechanically stable linkage is formed that allows the bacteria to stay on the tissue of the host (colonization) and to subsequently propagate locally. The adhesion to the host cell can be divided into two phases with different structures being involved in the interaction.

In the first phase of adhesion a contact between host cell and pathogen is mediated. Often cell appendage organelles, the so-called pili, are involved in mediating the contact. These cell organelles, which are also called fimbriae or fibrils, are few to several fine filamentous rigid or flexible appendages of the bacterial cell, which can be several times as long as the cell diameter. Therefore, there is no contact between the cell walls of pathogen and host cell in the pilus mediated adhesion. The majority of the known pili are heteropolymeric structures consisting of several components. The main subunit, which usually is present in many copies, fulfills the structural function, that is the framework function, whereas the actual adhesion function is fulfilled by side components, which usually are present in few copies.

A further form of adherence is the adhesion of pathogens to the host cells without the contribution of pili (pilus independent adherence, pia). In this case, the pathogen and the host cell are approaching each other, and finally the cell walls directly touch. This adhesion and stabilization of the contact between the cells takes place with the contribution of adhesines that are located in the bacterial cell wall. As a result of the direct contact between the cells, a signal is finally transmitted that initiates the pathogen induced phagocytosis and starts the invasion process into the target cell. The pia form of adherence can autonomically effect the adhesion of pathogens, for example in the case of pathogens lacking pili.

It can, however, also act as the second phase of adhesion, that is as the consecutive reaction after pilus mediated adhesion, and stabilize the contact between the cells. The adhesines that are involved in the pilus independent adhesion can but do not necessarily have to show different binding specifities from those that are involved in pilus dependent adhesion.

In the context of the invention the bacterial structures that are involved in the adhesion will in the following be called adhesines, those of the host cells will be called receptors. If there is no contact between adhesin and receptor, "defense mechanisms" of the host, such as fibrillation of the epithelia, mucus secretion, mass flow of body fluids and the like, eliminate the pathogens. The development of an infection is, therefore, prevented from the very beginning. Thus, a disturbance of the adhesion of the pathogens by means of inhibiting the interaction between adhesin and receptor of the target cell represents a very effective approach for preventing and treating infections. Such therapeutically effective approaches comprise the production of antibodies specifically blocking the adhesin function, either by active immunization (vaccination) or by administration of antibodies already existing (passive immunization). The adhesin receptor binding can, in the same way, be inhibited by means of passive administration of both receptor analogous and adhesin analogous substances. These substances competitively bind to the corresponding partner structures, thereby blocking their involvement in productive interactions. In the context of the invention such substances are called inhibitors.

The approaches using pilin, the main component of the pilus that fulfills the structural function, in order to develop a broadly effective vaccine effectively blocking the adhesion of pathogenic *Neisseria* have failed so far. The reason probably is that (i) pilin itself has no adhesin function and (ii) pilin possesses an especially distinct intra- and interstem specific antigenic variation. Since both limitations, as described above, do not apply to adhesins, the use of an adhesin as a vaccine is more promising.

The technical problem of the present invention therefore is to provide proteins and DNA molecules encoding them that serve as adhesion structures for *Neisseria* species or contribute to the development of such structures.

This problem is solved by providing the embodiments described in the claims.

Therefore, the present invention relates to nucleic acid molecules containing the nucleotide sequence described in Seq ID No. 1 or parts thereof with these nucleic acid molecules comprising one or more open reading frames encoding proteins or biologically active fragments thereof from bacteria of the genus *Neisseria* that mediate the adhesion of *Neisseria* cells to human cells. The term "reading frame" in this context is used synonymously with the term "coding region".

The subject matter of the invention also relates to nucleic acid molecules that basically show the nucleotide sequence described in Seq ID No. 1 but whereby the nucleotide sequences of the open reading frames deviate from those described in Seq ID No. 1 due to the degeneration of the genetic code. Preferably, the open reading frames of those nucleic acid molecules have nucleotide sequences encoding proteins with one of the amino acid sequences described in Seq ID No. 1.

The subject matter of the invention further relates to nucleic acid molecules hybridizing to the nucleic acid molecules described above and comprising coding regions encoding proteins that mediate the adhesion of *Neisseria* cells to human cells.

In the context of the present invention the term "hybridization" is used as described in Sambrook et al. (Molecular Cloning, A Laboratory Manual; Cold Spring Harbor Laboratory Press (1989), 1.101 to 1.104). Preferably, this term has the meaning of hybridization under stringent conditions. In particular, it has the meaning of a hybridization that still shows a positive hybridization signal after being washed for 1 h with 1×SSC and 0.1% SDS, preferably with 0.2×SSC and 0.1% SDS, at 55° C., preferably at 62° C. and most preferably at 68° C.

In a preferred embodiment the nucleic acid molecule of the invention originates from a pathogenic *Neisseria* species, in particular from *Neisseria gonorrhoea* or *Neisseria meningitidis*.

The term "nucleic acid molecule" as used here according to the invention relates to the polymeric form of nucleotides of any length, either as ribonucleotides or as desoxyribonucleotides. The term only relates to the primary structure of the molecule. In this sense, it comprises DNA and RNA molecules, in single- or double-stranded form. The DNA can either be cDNA or genomic DNA. The term further comprises the non-modified form as well as scientifically known modifications, e.g., methylation, capping, base substitution with natural or synthetic analogues, internucleotide modifications with uncharged compounds (e.g., methyl phosphate, phosphoamidate, carbamate, phosphotriester and the like) or with charged compounds (e.g., phosphorothioate, phosphorodithioate and the like) or with binding components such as proteins and peptides (e.g., nucleases, toxins, antibodies, poly-L-lysine, and the like). The term also comprises forms with intercalating substances (e.g., acridin, psoralen, and the like), chelators (e.g., with metals, radioactive metals or oxidizing metals and the like), with alkylating agents and finally with modified bonds (e.g., alpha anomeric nucleic acids, and the like).

The invention also relates to vectors containing a nucleic acid molecule of the invention. The vector can be any prokaryotic or eukaryotic vector. Examples of prokaryotic vectors are chromosomal vectors, such as bacteriophages (e.g., bacteriophage lambda, P1), and extrachromosomal vectors, such as plasmids with circular plasmids being particularly preferred. Suitable prokaryotic vectors are, for example, described in Sambrook et al. (see above), chapters 1 to 4. The vector according to the invention can also be a eukaryotic vector, for example a yeast vector or a vector suitable for higher cells (e.g., a plasmid vector, a viral vector, a plant vector, and the like). Examples of such vectors are also described in Sambrook et al. (see above, chapter 16). A vector containing a nucleic acid molecule of the invention is, for example, plasmid pES25 (contained in the *E. coli* strain H 2560 (DSM 10257)). The *E. coli* strain H 2560 was deposited on Sep. 18, 1995 with Deutsche Sammlung von Mikroorganismen (DSM) [German collection of microorganisms] in Brunswick, Federal Republic of Germany, as international recognized depositary authority in accordance with the stipulations of the Budapest Treaty on the International Recognition of the Deposit of Microorganisms for the Purpose of Patent Procedure under accession number DSM 10257.

The invention furthermore relates to host cells containing a vector as described above or being genetically manipulated with a nucleic acid molecule as described above. The term "host cell" in the context of this invention comprises both prokaryotic and eukaryotic host cells. Prokaryotic cells are preferred, particularly gram-negative prokaryotic cells, in particular *E. coli* cells. Suitable eukaryotic host cells are, for example, fungal cells (e.g., yeast cells), animal or plant cells.

The nucleotide sequence described in Seq ID No. 1 comprises three open reading frames. They represent an operon forming a functional unity. The three open reading frames called orfI, orfA and orfB encode three proteins that in the context of this invention are called OrfI, OrfA and OrfB. These sequences are responsible for the expression of a protein in *Neisseria* cells, in particular of the protein OrfA, which is involved in the adhesion of *Neisseria* cells to human cells. The proteins OrfI and OrfB obviously possess a regulatory function or a function as factors that are able to influence the functionality of OrfA.

This nucleic acid molecule therefore represents a region of the *Neisseria* genome that encodes proteins having the adhesin function of *Neisseria* cells.

The present invention further relates to nucleic acid molecules encoding a lipoprotein or biologically active fragments thereof from bacteria of the genus *Neisseria* having the amino acid sequence as described in Seq ID No. 2. In a preferred embodiment the invention relates to nucleic acid molecules encoding a protein having the amino acid sequence from the amino acid residue 19 to the amino acid residue 320 of the amino acid sequence as described in Seq ID No. 2. Such nucleic acid molecules preferably have the nucleotide sequence described in Seq ID No. 2, in particular the nucleotide sequence from nucleotide 189 to nucleotide 1095 of the sequence described in Seq ID No. 2.

The subject matter of the invention also relates to nucleic acid molecules encoding a lipoprotein from bacteria of the genus *Neisseria* whereby their nucleotide sequence deviates from the nucleic acid molecules described above due to the degeneration of the genetic code.

Furthermore, the present invention relates to nucleic acid molecules encoding a lipoprotein from bacteria of the genus *Neisseria* and hybridize to one of the nucleic acid molecules described above (for the definition of the term "hybridization" see above).

The subject matter of the invention also relates to fragments, derivatives and allelic variants of the nucleic acid molecules described above that encode the lipoprotein described above. Fragments are understood to be parts of the nucleic acid molecules that are long enough to encode the protein described. The term derivative in this context means that the nucleotide sequences of these molecules differ at one or more positions from the sequences of the nucleic acid molecules described above and that they show a high level of homology to these nucleotide sequences. Homology means a sequence identity of at least 40%, in particular an identity of at least 60%, preferably of more than 80% and particularly preferred of more than 90%. The deviations to the nucleic acid molecules described above can be caused by deletion, substitution, insertion or recombination.

Homology further means that there is a functional and/or structural equivalence between the corresponding nucleic acid molecules or the proteins encoded by them. The nucleic acid molecules that are homologous to those described above and that represent derivatives of these nucleic acid molecules usually are variants of these molecules displaying modifications that have the same biological function. They can be naturally occurring variants, for example sequences from other organisms, or mutations, which either occur naturally or that have been introduced by means of specific mutagenesis. Furthermore, the variants can be synthetically produced sequences.

The allelic variants can be both naturally occurring variants or variants that were synthetically produced or that were produced by recombinant DNA techniques.

The proteins encoded by the various variants of the nucleic acid molecules according to the invention show certain common characteristics, for example enzyme activity, molecular weight, immunological reactivity, conformation etc., as well as physical properties such as the electorphoretic mobility, chromatographic behavior, sedimentation coefficients, solubility, spectroscopic properties, stability, pH optimum, temperature optimum etc.

Preferably, the proteins encoded by the nucleic acid molecules according to the invention show a homology of 80%, particularly preferred of more than 90% to the nucleotide sequence described in Seq ID No. 2.

The nucleic acid molecules described above encode a lipoprotein from bacteria of the genus *Neisseria*. This protein is called OrfA in the context of the present invention. This protein is, according to experimental data, located on the cell surface of *Neisseria* cells, in particular on the outer membrane. The protein preferably has a molecular weight of about 36 kd if it is analyzed in the T7 expression system.

Furthermore, this protein possesses a biological activity that mediates the adhesion of *Neisseria* cells to human cells. This is in particularly made because this protein forms a complex with the protein from *Neisseria* known as PilC. The adhesion preferably takes place on human epithelial cells.

Furthermore, the invention relates to vectors containing nucleic acid molecules described above. Examples of such vectors have already been described above.

In a preferred embodiment the DNA molecules according to the invention are linked in such vectors with regulatory DNA elements that make the expression of the protein in prokaryotic or eukaryotic cells possible. Examples thereof are in the context of this invention promoters, operators, enhancers and the like.

Furthermore, the invention relates to host cells that contain vectors according to the invention described above or that have been genetically manipulated with the nucleic acid molecules described above. Genetically manipulated means that such a molecule has been introduced into the host cell or in a precursor cell by means of (gene) technological methods. Again, the above-described host cells are suitable.

The invention also relates to methods for the production of the described lipoprotein or a biologically active fragment thereof whereby the host cells described above are cultivated under conditions that allow the expression of the protein and the protein is isolated from the cells and/or the culture supernatant.

The invention also relates to proteins encoded by one of the nucleic acid molecules described above, as well as to biologically active fragments thereof as well as to proteins available by the method described above. In particular, the invention relates to proteins having amino acid sequences that immunologically cross-react with the described proteins. The term "protein" comprises in the context of the present invention also naturally occurring variants or modifications or fragments or synthetically produced modifications, variants or fragments with the corresponding biological activity. Derived or recombinant proteins do not necessarily have to be biologically translated from the nucleotide sequence. They can be produced in any way, including chemical synthesis, in vitro synthesis by means of an expression system or by isolation from organisms. Proteins according to the invention can contain one or more amino acid analogues or amino acids not naturally occurring. Also, modifications (e.g., glycosylation, and the like) or labeling (e.g., biotinylation) according to the scientific knowledge can be contained.

The fragments preferably have a length of at least 3 to 5 amino acids, particularly preferred of 8 to 10 amino acids and in particular preferred of 11 to 15 amino acids. This is also true for the proteins according to the invention described below.

The lipoprotein OrfA according to the invention can be purified, for example, by a method that is based on the interaction of this protein with the PilC protein from *Neisseria gonorrhoeae*. It is preferably purified from homogenates of cells expressing this protein by means of chromatography matrices containing immobilized PilC protein. The protein can then be selectively eluted using its affinity to PilC and produced in essentially pure form.

The proteins according to the invention or fragments thereof can be used as immunogens for the production of antibodies. Therefore, the present invention also relates to antibodies that are directed against a protein according to the invention or a fragment thereof. The antibodies can be both polyclonal and monoclonal. Methods for the production of such antibodies are known to the skilled person.

In a preferred embodiment such antibodies are directed against epitopes of the protein according to the invention or fragments thereof that are important for the adherence and for the interaction with PilC.

The antibodies according to the invention can be, for example, produced by introducing the nucleic acid sequences according to the invention described above into hosts by in vivo transfection. Thereby, the protein or a fragment thereof is expressed in the host and the antibodies directed against them are induced (nucleic acid vaccination). This is also the case with the antibodies described below.

The present invention further relates to nucleic acid molecules having a length of at least 12 nucleotides and specifically hybridizing to the nucleic acid molecule described above. Preferably, such nucleic acid molecules have a length of at least 15 nucleotides, particularly preferably of 20 nucleotides. Such molecules are, for example, suitable as primers for in vitro amplification, for example by polymerase chain reaction (PCR), or suitable for diagnostic purposes, that is for specifically identifying the nucleic acid molecules of the invention in samples.

The invention further relates to pharmaceutical compositions containing a nucleic acid molecule according to the invention described above, a protein, a biologically active fragment thereof and/or an antibody according to the invention described above. In the context of the present invention such pharmaceutical compositions can contain the usual pharmaceutical adjuvants, diluents, additives and/or carriers. The invention also relates to vaccines containing the nucleic acid molecules described above, proteins, biologically active fragments thereof and/or antibodies.

In a further aspect the present invention relates to diagnostic compositions containing the nucleic acid molecules according to the invention described above, proteins, biologically active fragments thereof and/or antibodies.

A further aspect of the present invention relates to receptors and substances having receptor function, interacting as ligands with the adhesin according to the invention, the OrfA-PilC complex. Such substances can be identified as competitive inhibitors of the adherence function due to their interaction with the OrfA-PilC complex. They can be surface components of human cells, particularly preferred surface components of human epithelial cells or chemical substances of any origin.

Finally, the present invention relates to inhibitors that influence the interaction between the OrfA-PilC adhesin complex and its receptors. Enclosed are all substances according to the invention that influence the interaction between the OrfA-PilC adhesin and its cellular receptor and therefore disturb the adherence. In a particularly preferred embodiment substances that irreversibly bind to the adhesin complex such as receptor analogues are encompassed.

Finally, the present invention relates to pharmaceutical compositions containing as an agent
(a) a receptor according to the invention;
(b) a receptor analogue according to the invention; and/or
(c) an inhibitor according to the invention,
optionally together with the usual pharmaceutical adjuvants, diluents, additives and carriers.

The pharmaceutical compositions described in the context of the present invention can be used for identifying and characterizing a bacterial sample not yet known as pathogenic *Neisseria* spc. and for diagnosing a *Neisseria* infection.

On the polynucleotide level, preferably hybridization probes are used containing the nucleotide sequences of the invention that are specific for one of the orf-gene regions or nucleotide sequences of the invention from one of the orf gene regions are used as primers for the PCR amplification of the genomic DNA region to be identified that is specific for pathogenic *Neisseria*.

On the polypeptide level diagnosis is preferably performed with the help of antibodies of the invention or, in the case of antibody screening tests, with the help of immunogenic proteins of the invention or fragments thereof.

Receptors, receptor analogous substances and inhibitors of the interaction between the OrfA of the invention and the corresponding receptors of the host cells can be used as therapeutics for infections at an early stage or if an infection is suspected. By strongly inhibiting the adherence, the adhesion of the pathogens to the epithelial host cells can be prevented so that by the usual defense mechanisms, such as ciliary movement of the epithelial cells, mucus secretion, mass flow of body fluids and the like, the pathogens can be eliminated.

Finally, the pharmaceutical compositions of the invention can be used for preventing or fighting *Neisseria* infections. Preferably, for preventive applications the proteins of the invention or fragments thereof are used for the production of a vaccine for active immunization, or antibodies of the invention are used for the production of a passive vaccine applicable as a therapeutic. The applications described above also apply to the pharmaceutical compositions and diagnostic compositions described below.

The subject matter of the invention further relates to nucleic acid molecules encoding a protein or a biologically active fragment thereof from bacteria of the genus *Neisseria* having the amino acid sequence described in Seq ID No. 3. Such nucleic acid molecules preferably have the nucleotide sequence described in Seq ID No. 3, in particular the one of the described coding region. The invention also relates to nucleic acid molecules the sequence of which deviates from the sequences of the molecules mentioned above due to the degeneracy of the genetic code. Also nucleic acid molecules are the subject matter of the invention that hybridize to the nucleic acid molecules mentioned above (for the definition of the term "hybridization" see above). For the possible variants of the nucleic acid molecules the same is true what has already been described in connection with the nucleic acid molecules encoding OrfA.

The invention also relates to vectors containing the described nucleic acid molecules, in particular those in which they are linked to regulatory DNA elements for the expression in prokaryotic or eukaryotic cells, as well as to host cells that contain such vectors or that are genetically manipulated with the described nucleic acid molecules.

The invention also relates to proteins encoded by the nucleic acid molecules described above and to proteins containing amino acid sequences that immunologically cross-react with the amino acid sequence depicted in Seq ID No. 3 or fragments thereof. In the context of this invention they are called OrfI proteins. The protein from *Neisseria gonorrhoeae* having the amino acid sequence depicted in Seq ID No. 3 shows in the T7 expression system an apparent molecular weight of about 18 kd. A homology to presently known proteins could not be shown. Experimental data indicate that the protein is located intracellularly and possibly has a regulatory function.

This protein can be produced by a method in which a host cell described above is cultivated under conditions allowing the expression of the protein and in which the protein is obtained from the cells and/or the culture supernatant. Therefore, the invention also relates to proteins obtainable by such a method.

The invention also relates to antibodies against a protein described above or a fragment thereof as well as to nucleic acid molecules having a length of at least 12 nucleotides and specifically hybridizing to a nucleic acid molecule described above. Preferably, the molecules have a length of more than 15 nucleotides and particularly preferably of more than 20 nucleotides.

The invention further relates to pharmaceutical compositions containing a nucleic acid molecule, protein, biologically active fragment thereof and/or an antibody described above and, optionally, a pharmaceutically acceptable carrier.

The invention further relates to diagnostic compositions containing the nucleic acid molecules, proteins, biologically active fragments thereof and/or antibodies described above.

The subject matter of the invention further relates to nucleic acid molecules encoding a protein or a biologically active fragment thereof from bacteria of the genus *Neisseria* that has the amino acid sequence depicted in Seq ID No. 4. Such nucleic acid molecules preferably have the nucleotide sequence depicted in Seq ID No. 4, in particular the one of the indicated coding region. The invention also relates to nucleic acid molecules the sequences of which deviate from the nucleotide sequence of the above-mentioned molecules due to the degeneration of the genetic code. Furthermore, the subject matter of the invention also relates to nucleic acid molecules hybridizing to the above-mentioned nucleic acid molecules (for the definition of the term "hybridization" see above). The same applies to possible variants of the nucleic acid molecules as has already been described in connection with the nucleic acid molecules encoding OrfA.

In a preferred embodiment the above-described nucleic acid molecules encode a protein that is able to form a complex with the protein PilC and therefore shows an ability of adherence to human cells.

The invention also relates to vectors containing the described nucleic acid molecules, in particular those in which they are linked to regulatory DNA elements for the expression in prokaryotic or eukaryotic cells, as well as to host cells that contain such vectors or that have been genetically manipulated with the above-described nucleic acid molecules.

The invention also relates to proteins encoded by the above-described nucleic acid molecules and to proteins containing the amino acid sequences that immunologically cross-react with the amino acid sequence depicted in Seq ID No. 4 or parts thereof. These are called OrfB in the context of the present invention. The protein from *Neisseria gonorrhoeae* having the amino acid sequence depicted in Seq ID No. 4 shows in the T7 expression system an apparent molecular weight of about 57 kd. A homology to presently known proteins could not be shown. Experimental data indicate that the protein is, like OrfA, located at the cell surface and is accessible from the outside. Furthermore, it obviously also possesses the ability to form a complex with the protein PilC and to induce either alone or in combination with OrfA the adhesion to human cells.

This protein can be produced by a method in which an above-described host cell is cultivated under conditions allowing the expression of the protein and in which the protein is obtained from the cells and/or the culture supernatant. Therefore, the invention also relates to proteins obtainable by such a method.

The invention also relates to antibodies against an above-described protein or fragment thereof, as well as to nucleic acid molecules having a length of at least 12 nucleotides and specifically hybridizing to an above-described nucleic acid molecule. Preferably, such molecules have a length of more than 15 nucleotides and particularly preferred of more than 20 nucleotides.

Furthermore, the invention relates to pharmaceutical compositions containing an above-described nucleic acid molecule, protein, biologically active fragment thereof and/or antibody and, optionally, pharmaceutically acceptable carriers.

The subject matter of the invention further relates to diagnostic compositions containing the above-described nucleic acid molecules, proteins, fragments thereof and/or antibodies.

ILLUSTRATION OF THE FIGURES AND THE SEQUENCE PROTOCOLS

FIG. 1 schematically shows the construction of the plasmid pES25.

FIGS. 2A-2C show the nucleotide sequence (SEQ ID No. 1) of the orf gene region, starting from position 1 at the modified Bgll cleavage site and ending with position 3260, the last nucleotide of the HindIII cleavage site. Restriction cleavage sites, ribosome binding sites (Shine-Dalgarno sequences) and promoter sequences (−35 and −10 regions) are labeled.

SEQ ID No. 1 further shows the amino acid sequences of the proteins OrfI (SEQ ID NO: 6), OrfA (SEQ ID NO: 5) and OrfB (SEQ ID NO: 7) encoded by the orf gene region (SEQ ID NO:1 extends over FIGS. 2A-2C). The amino acids of the lipoprotein signal sequence of OrfA are written in italic, the cleavage sites of the lipoprotein signal peptidase II is labeled with the tip of an arrow. The amino acid cysteine that represents the amino terminal of the processed OrfA lipoprotein and is modified to glyceryl cysteine with fatty acid is marked with a circle. The first seven amino acids of OrfB that are similar to a typeIV-pilin-signal sequence are written in bold. The labeling between amino acids 7 and 8 and between 11 and 12 characterize potential cleavage sites analogous to the processing of the typeIV-pilin.

Seq ID No. 2 shows the nucleotide sequence of the gene region encoding OrfA as well as flanking sequences (SEQ ID NO:2 extends from FIGS. 2A and 2B, as indicated). The amino acid sequence of OrfA is depicted, too (SEQ ID NO: 5).

Seq ID No. 3 shows the nucleotide sequence of the gene region encoding OrfI as well as flanking sequences (SEQ ID NO:3 is indicated in FIG. 2A). The amino acid sequence of OrfI is depicted, too (SEQ ID NO: 6).

Seq ID No. 4 shows the nucleotide sequence of the gene region encoding OrfB as well as flanking sequences (SEQ ID NO:4 extends over FIGS. 2B and 2C, as indicated). The amino acid sequence of OrfB is depicted, too (SEQ ID NO: 7).

The examples illustrate the invention.

EXAMPLES

Example 1

Method for the Isolation of the Lipoprotein Adhesin OrfA

During the chromatographic purification of the PilC protein a decisive observation with regard to the identification of the new adhesin of Neisseria gonorrhoeae of the invention was made. A recombinant PilC protein was used that was amplified by an oligo-histidine region with six histidine residues ($His_6$-tag) in order to make the chromatographic purification easier (Rudel et al., Nature 373, 357-359, 1995). The amplification of the protein by the histidine hexapeptide makes the selective binding to a nickel-nitrilotriacetate-agarose matrix (Ni-NTA matrix) possible. After the cell wall fraction produced from cultures of a pilus-free PilC overexpression strain N560 (Rudel et al., see above) from Neisseria gonorrhoeae had been extracted, the extract was loaded on an Ni-NTA chromatography matrix. Usually, for the method that was developed for the purification of recombinant PilC unspecifically bound material was removed by extensive washing with a buffer containing imidazole. However, in the first elution fraction a protein of 36 kd (OrfA) could be identified together with PilC in an approximately equimolar ratio.

For the preparation of the PilC-OrfA protein fraction the strain N560 from Neisseria gonorrhoeae was plated on 30 GC-agar plates and incubated in 5% $CO_2$ at 37° C. for 20 hours. The GC-agar medium (GC agar base, Becton Dickinson, Heidelberg) contained the usual additional factors necessary for the growth of Neisseria gonorrhoeae (0.1 mg vitamin B12, 10 mg adenine, 0.3 mg guanine, 100 mg glutamine, 1 mg cocarboxylase, 0.3 mg thiamine, 259 mg L-cysteine, 11 mg L-cystine, 1.5 mg arginine, 5 mg uracil, 0.2 mg $Fe(NO_3)_3$, 2.5 mg nicotineamide-adenine dinucleotide, 0.13 mg p-aminobenzoic acid and 1 g dextrose per 1 liter of medium) that were added as a sterile filtrate to the GC basis medium after heat sterilization. Furthermore, the so supplemented GC agar medium contained 5 µg/ml tetracycline and 100 µM IPTG. The bacterial lawns were removed with cotton pads, transferred to 30 ml of washing buffer (Tris-HCl pH 8.0 with 0.15 M NaCl) and centrifuged at 4,000 rpm, 4° C. for 15 minutes (Du Pont Sorvall Centrifuge RC-5B, Rotor SS-34). The cell sediment was again resuspended in 30 ml of washing buffer, and the bacteria were broken up by ultrasonic homogenization after lysozyme and 5 mM EDTA $Na_2$ had been added. Intact bacteria were separated by centrifugation at 5,000 rpm at 4° C. for 15 minutes. The cell coats of the lysed bacteria were sedimented by centrifugation of the supernatant at 20,000 rpm at 4° C. for 60 minutes and taken up in 10 ml of washing buffer additionally containing 10% glycerine, 10 mM $MgCl_2$ and 2% Triton X-100. After an incubation of 45 minutes at 37° C. they were centrifuged again (20,000 rpm, 4° C. for 60 minutes) and the membrane sediment suspended in 10 ml of washing buffer with 10% glycerine, 10 mM $MgCl_2$ and 2% LDAO (N,N-Dimethyldodecylamin-N-oxide) and incubated at 37° C. for 60 minutes. After they were centrifuged again (20,000 rpm, 4° C. for 60 minutes), the supernatant containing the biologically active PilC-OrfA complex was subjected to a nickel-chelate-affinity chromatography for further purification. For this purpose a Ni-NTA-gel matrix (300 ml bed volume) was washed with 5 bed volumes of aqua bidest. and loaded with 10 ml of the supernatant. Unspecifically bound proteins were removed by elution with 5 column volumes of 50 mM imidazole in PBS buffer pH 8.0. After the column had been washed again with 5 to 10 bed volumes 20 mM sodium phosphate pH 7.5 with 0.15 M NaCl (PBS buffer) the biologically active PilC-OrfA complex was eluted with a citrate/phosphate buffer (10 mM citric acid, 1 M sodium phosphate, pH 3.5, 10% glycerin, 0.15 M NaCl) in the first elution fraction and instantly neutralized with a 1 M $Na_2HPO_4$ solution. The eluate containing PilC and OrfA was frozen in liquid nitrogen and stored at −70° C.

Example 2

Isolation of the Polynucleotide Sequence Carrying the Orf-Gene Region

To further characterize the 36 kd OrfA protein, mice were immunized with the PilC-36 kd protein fraction. The 36 kd protein proved to be very immunogenic. With the antibodies obtained this way a pBA plasmid gene library of the Neisseria gonorrhoeae MS11 genome in E. coli GC1 was screened for the presence of antigens. Several clones showing a positive reaction were isolated and clone H1967 was chosen for further characterization.

The library plasmid pES25 (FIG. 1) of clone H1967 contained a genomic fragment of approximately 11 kb, cloned in vector pBA. Restriction fragments of the total region were subcloned in pUC and pBluescript KS (+) vectors, respectively. On the basis of the expression of the derived plasmids in minicells and immunoblotting analyses subclones were chosen producing the 36 kd protein. The subclones were used for sequencing. The sequences were determined by directly sequencing restriction fragments, by sequencing continuously shortened ExoIII nuclease fragments of the BglI-PstI fragment (positions 1 to 2560 of Seq ID No. 1), as well as by sequencing PCR amplified fragments.

The region depicted in SEQ ID No. 1 starting from the BglI cleavage site (position 1) to the HindIII cleavage site (position 3260) had three open reading frames with a high coding probability with each reading frame beginning with the start codon ATG, having a ribosome binding site that precedes the start codon in a suitable distance (S.D. sequence) and ending with a stop codon.

The three reading frames have the same orientation. The first open reading frame starts at position 136 of the sequence depicted in SEQ ID No. 1 and ends at position 450 with the stop codon TAA. The encoded protein was called OrfI and had an apparent molecular weight of 18 kd in the T7 expression system.

No significant homologues could be identified by sequence comparison in the EMBL gene library (Release 43.0 from 6/95) and in the SwissProt data bank (Release 31.0 from 3/95), neither on a nucleotide sequence level nor on an amino acid sequence level.

The second open reading frame starts at position 583 and ends at position 1545 with the stop codon TGA. It encodes the OrfA protein having an apparent molecular weight of 36 kd in the T7 expression system. Also to this sequence no significant homologues could be detected via data base search. The sequence analysis by means of the protein analysis program "Motifs" (GCG Genetics Computer Group, Inc., Madison, Wis., USA) showed, however, a complete homology of the N-terminus of OrfA to lipoprotein specific signal sequences (position 583 to 636). The characterization of OrfA as a lipoprotein could be substantiated by experiments (vide infra).

The third open reading frame starts at position 1585 and ends at position 3114 with the stop codon TGA. The protein OrfB hereby encoded has an apparent molecular weight of 57 kd in the T7 expression system. Also to this reading frame no homologue could be identified via data base search.

As a structural peculiarity the amino terminus of the OrfB sequence displays a signal sequence showing similarities to the type IV-prepilin signal sequence. At positions 8 and 12 of the amino acid sequence there is phenylalanine so that there are in addition two possible cleavage sites for the type IV pilin signal peptidase. It can be derived herefrom that OrfB presumably is a secreted protein.

The molecular weights of all the three gene products measured in the T7 expression system correspond to the values theoretically calculated from the sequence. The separation of the expression products by means of gel electrophoresis showed that the OrfB-band was significantly weaker than the OrfA-band in all the cases. This points to a weaker expression of OrfB.

Two regions showing a sequence homology to the promoter regions were identified. One of them is located in front of the orfI gene, the second one in front of the orfA gene, each leaving an appropriate distance (SEQ ID No. 1). Therefore, it can be assumed that orfA and orfB form a transcription unity.

The analysis of the *Neisseria gonorrhoeae* MS11 genome after ClaI and MluI digestion showed a complex band pattern in Southern hybridization with plasmid pES-8 as sample. This fact indicates the existence of several copies of the orf-gene region, probably of three copies, in the genome of *Neisseria gonorrhoeae* MS11. If all these loci are expressed, if they are subjected to antigenic variations like, for example, the *Neisseria* genes pilS and opa, and if the flanking regions of the orf gene region are involved in the sequence repetitions, is presently not known.

Example 3

Characterization of the Localization of OrfA and OrfB on the Cell Surface

In order to experimentally prove the lipoprotein nature of orfA derivable from the perfect structure homology of the amino terminus of orfA to lipoprotein signal sequences, both *N. gonorrhoeae* and *E. coli* recombinants transformed with the orf-gene region were labeled with [$^3$H] palmitate. The results of the labeling show that in all the cases, both with *N. gonorrhoeae* and with the *E. coli* recombinants, lipoproteins in the corresponding molecular weight range could be identified. While with *N. gonorrhoeae* several proteins were labeled and the labeled band could not be precisely assigned since there was no orfA$^-$ mutant available, the orfA recombinants of *E. coli* showed in comparison to the control strain unambiguously only one additional band having the molecular weight of OrfA. An OrfA fusion protein that was tested in addition and was amplified at the carboxy-terminal by a fusion of 3 kd, also had a [$^3$H] palmitate labeling and migrated to a position precisely corresponding to the molecular weight that was, as expected, increased due to the fusion.

When prepared cell coats were treated with detergents, OrfA showed a solubility that is typical of proteins of the outer membrane. By separating the cell coat by means of density-gradient centrifugation it could be confirmed by means of marker proteins that OrfA was located in the outer membrane of *N. gonorrhoeae*. Also with orf recombinants of *E. coli*, OrfA was shown to be a protein component of the outer membrane by means of said method.

The accessibility of the cell surface was proven by means of an immunofluorescence test both for OrfA and OrfB. A defective pilC mutant of *Neisseria gonorrhoeae* the two pilC genes of which were switched off is labeled by the PilC-OrfA antiserum in the same way as recombinant *E. coli* strains carrying the orf-gene region. The non-transformed control strain showed, as was to be expected, a negative reaction. A positive reaction in the immunofluorescence test of *N. gonorrhoeae* and orf recombinant *E. coli* strains could be brought about by means of OrfA and OrfB specific antisera using purified fusion proteins of either OrfA or OrfB for the production of these antisera. If antisera were used directed against an OrfI fusion protein, the immunofluorescence test with *N. gonorrhoeae* was negative. From this it can be deduced that OrfA and OrfB are located on the cell surface and are accessible from the outside, whereas OrfI probably is located intracellularly.

The surface localization of OrfA and OrfB could only be proven in recombinant *E. coli* strains carrying the whole orf region.

Example 4

Adhesin Property of the OrfA-PilC Complex

As mentioned above OrfA could be obtained in pure form by chromatography on an Ni-NTA-chelate matrix due to its affinity to PilC. Since the function of PilC as pilus associated adhesin had been proven and the direct binding of PilC to human ME-180 cells had been known, it was obvious to test the adherence property of the PilC-OrfA complex. The experiments were performed with the *E. coli* strain HB101 (E141) since it does not possess the mannose specific typeI pili and shows almost no binding to human ME-180 and Chang epithelial cells. After the transformation of HB101 with the plasmid pES25, no adherence, neither to ME-180 nor to Chang cells, could be mediated. If the same recombinants, however, were pre-incubated with PilC protein, a strong adherence to Chang epithelial cells but not to ME-180 cells could be induced (Table I).

TABLE I

OrfA-dependent modulation of the PilC mediated adhesin function

| | Adherence to human epithelial cells | |
|---|---|---|
| | ME180 cells | Chang cells |
| *N. gonorrhoeae*, Orf+ PilC+, Pili+ | +++ | + |
| *N. gonorrhoeae*, Orf+, PilC+, Pili− | + | +++ |
| *E. coli* (E141) | − | − |
| *E. coli* (E141) + PilC (extern) | − | − |
| *E. coli* (H2561) | − | − |
| *E. coli* (H2561) + PilC (extern) | − | − |
| *E. coli* (H2560) | − | + |
| *E. coli* (H2560) + PilC (extern) | − | +++ |

Three independent experiments were evaluated, whereby the adherence of *Neisseria* was determined using 500 cells and the adherence of the *E. coli* strains was determined per epithelial cell.

+++100%, ++50%, +25% adherence.

*E. coli* E141=*E. coli* strain HB101 without plasmid; *E. coli* H2561=*E. coli* strain HB101 with plasmid pBA; *E. coli* H2560=*E. coli* strain HB101 with plasmid pES25

The plasmid pES25 (FIG. 1) is a pBA vector containing a genomic fragment from Neisseria gonorrhoeae of approximately 11 kb carrying the coding regions orfA, orfB and orfI.

The E. coli strain H2560 was deposited at the Deutsche Sammiung für Mikroorganismen (DSM, Braunschweig, Germany) under the DSM-Accession Number DSM 10257.

The result obtained is surprising since pilus carrying Neisseria bind to ME-180 cells with a significantly higher affinity than to Chang epithelial cells. This result can be put down to the fact that PilC has different adherence properties depending on its localization. As an adhesin component in the pilus PilC preferably binds to receptors of the ME-1800 cell surface, whereas as an adhesin located on the cell surface in the complex with OrfA PilC preferably recognizes receptors on Chang epithelial cells. If in the latter case adhesin properties also can be ascribed to OrfA and/or OrfB, is presently not known.

The results obtained for recombinant E. coli strains could be reproduced with the same result with N. gonorrhoea. If the pilus-free strain N 300 (P-Opa-), which hardly binds to ME-180 or Chang cells, is pre-incubated with purified PilC, the adherence to Chang epithelial cells can be significantly increased.

The described experimental approaches obviously provide for a model that is suitable to analyze a mechanism for the modulation of the adherence properties, how they can in cascade-like order effect the increasingly strong adherence of the pathogens to the host cells or how they can be the basis for the tissue tropism.

What is claimed:

1. An isolated nucleic acid molecule encoding a lipoprotein or a biologically active fragment of said lipoprotein that mediates adhesion of *Neisseria* cells to human cells from a bacteria of the genus *Neisseria*, selected from the group consisting of
   (a) an isolated nucleic acid molecule that is a fragment of SEQ ID NO:1 and encoding a protein comprising SEQ ID NO:5;
   (b) an isolated nucleic acid molecule encoding a protein sharing 95% sequence identity with a fragment of SEQ ID NO:1 encoding SEQ ID NO:5 due to the degeneracy of the genetic code;
   (c) an isolated nucleic acid molecule comprising a nucleotide sequence that hybridizes under stringent hybridization conditions of 0.2×SSC, 0.1% SDS and 68° C. to
       (i) the complement of a nucleotide sequence that is a fragment of SEQ ID NO:1 encoding a protein comprising SEQ ID NO:5,
       (ii) the complement of a nucleotide sequence which is 95% identical to a nucleotide sequence that is a fragment of SEQ ID NO:1 encoding a protein comprising SEQ ID NO:5.

2. The isolated nucleic acid molecule according to claim 1, wherein the nucleic acid molecule originates from a pathogenic *Neisseria* species.

3. The isolated nucleic acid molecule according to claim 2, wherein the *Neisseria* species is *Neisseria gonorrhoeae* or *Neisseria meningitidis*.

4. The isolated nucleic acid molecule according to claim 1, wherein the lipoprotein or biologically active fragment of said lipoprotein has the ability to adhere to human cells.

5. A vector comprising the isolated nucleic acid molecule according to claim 1.

6. The vector according to claim 5, wherein the isolated nucleic acid molecule is operatively linked to at least one regulatory DNA element allowing the expression of said isolated nucleic acid molecule in a prokaryotic or an eukaryotic cell.

7. A recombinant host cell comprising the vector according to claim 5.

8. A recombinant host cell comprising the isolated nucleic acid molecule according to claim 1.

9. An isolated nucleic acid molecule having a length of at least 12 nucleotides specifically hybridizing under stringent hybridization conditions of 0.2×SSC, 0.1% SDS and 68° C. to the isolated nucleic acid molecule according to claim 1.

10. The vector according to claim 5, wherein the vector is a plasmid.

* * * * *